(12) United States Patent
Oakley et al.

(10) Patent No.: US 8,924,230 B2
(45) Date of Patent: *Dec. 30, 2014

(54) DATA MANAGEMENT APPARATUS FOR COMPARING PATIENT DATA WITH AILMENT ARCHETYPES TO DETERMINE CORRELATION WITH ESTABLISHED AILMENT BIOMARKERS

(75) Inventors: David Oakley, Boulder, CO (US); Michael Hickey, Boulder, CO (US)

(73) Assignee: WAVi, Boulder, CO (US)

( * ) Notice: Subject to any disclaimer, the term of this patent is extended or adjusted under 35 U.S.C. 154(b) by 43 days.

This patent is subject to a terminal disclaimer.

(21) Appl. No.: 12/889,682

(22) Filed: Sep. 24, 2010

(65) Prior Publication Data

US 2011/0099026 A1    Apr. 28, 2011

Related U.S. Application Data

(63) Continuation-in-part of application No. 12/567,249, filed on Sep. 25, 2009, which is a continuation-in-part of application No. 12/505,185, filed on Jul. 17, 2009.

(51) Int. Cl.
| | |
|---|---|
| G06Q 50/24 | (2012.01) |
| G06F 19/00 | (2011.01) |
| A61B 5/00 | (2006.01) |
| G06Q 50/22 | (2012.01) |
| G06Q 10/10 | (2012.01) |
| A61B 5/0476 | (2006.01) |
| A61B 5/04 | (2006.01) |

(52) U.S. Cl.
CPC .............. *G06Q 50/22* (2013.01); *G06F 19/3443* (2013.01); *A61B 5/4821* (2013.01); *A61B 5/0006* (2013.01); *G06Q 10/10* (2013.01); *G06F 19/324* (2013.01); *A61B 5/0476* (2013.01); *G06F 19/322* (2013.01); *A61B 5/04017* (2013.01)
USPC ........................................................... 705/2

(58) Field of Classification Search
USPC ............................................................. 705/2
See application file for complete search history.

(56) References Cited

U.S. PATENT DOCUMENTS

| | | |
|---|---|---|
| 5,038,782 A | 8/1991 | Gevins et al. |
| 5,479,934 A | 1/1996 | Imran |

(Continued)

FOREIGN PATENT DOCUMENTS

| | | |
|---|---|---|
| WO | WO-0051028 A1 | 8/2000 |
| WO | WO-2009079377 A2 | 6/2009 |

OTHER PUBLICATIONS

International Search Report dated Jul. 7, 2011, in related Application No. PCT/US2010/049840, 5 pages.

(Continued)

*Primary Examiner* — John Pauls
(74) *Attorney, Agent, or Firm* — Squire Patton Boggs (US) LLP

(57) ABSTRACT

The Patient Data Management System operates under the control of a physician to implement a patient-specific instance of the apparatus which is capable of accessing at least one data manipulation module, each defining at least one process for transforming patient medical data pursuant to a predefined schema. A patient medical data processor is responsive to the physician selecting a set of patient medical data, at least one of the data manipulation modules, and an order of applying the selected data manipulation modules to the selected patient medical data for processing the selected patient medical data using the selected data manipulation modules in the selected order to identify data indicative of a predetermined condition in the selected patient medical data. A display is available for presenting a visualization of the data indicative of a predetermined condition in the selected patient medical data.

20 Claims, 16 Drawing Sheets

(56) References Cited

U.S. PATENT DOCUMENTS

| | | | |
|---|---|---|---|
| 6,167,298 | A | 12/2000 | Levin |
| 6,195,576 | B1 | 2/2001 | John |
| 6,381,481 | B1 | 4/2002 | Levendowski et al. |
| 6,912,414 | B2 | 6/2005 | Tong |
| 7,447,643 | B1 * | 11/2008 | Olson et al. .................. 705/2 |
| 2002/0188216 | A1 | 12/2002 | Kayyali et al. |
| 2003/0023183 | A1 | 1/2003 | Williams |
| 2003/0232396 | A1 | 12/2003 | Mathew et al. |
| 2003/0233250 | A1 | 12/2003 | Joffe et al. |
| 2009/0088619 | A1 | 4/2009 | Turner et al. |
| 2009/0150183 | A1 * | 6/2009 | Schmitt et al. ................ 705/3 |
| 2009/0182242 | A1 | 7/2009 | Moses et al. |
| 2010/0010831 | A1 | 1/2010 | Fueyo et al. |

OTHER PUBLICATIONS

In the US Patent and Trademark Office U.S. Appl. No. 12/505,185 Final Office Action dated Mar. 20, 2012, 14 pages.
In the US Patent and Trademark Office U.S. Appl. No. 12/505,185 Non-Final Office Action dated Oct. 12, 2011, 12 pages.
In the US Patent and Trademark Office U.S. Appl. No. 12/505,185 Non-Final Office Action dated Oct. 24, 2012, 13 pages.
In the US Patent and Trademark Office U.S. Appl. No. 12/567,249 Final Office Action dated Mar. 23, 2012, 10 pages.
In the US Patent and Trademark Office U.S. Appl. No. 12/567,249 Non-Final Office Action dated Nov. 7, 2011, 7 pages.
In the US Patent and Trademark Office U.S. Appl. No. 12/567,249 Non-Final Office Action dated Nov. 7, 2012, 9 pages.
In the US Patent and Trademark Office U.S. Appl. No. 12/889,655 Non-Final Office Action dated Aug. 31, 2012, 9 pages.
In the US Patent and Trademark Office U.S. Appl. No. 12/889,697 Final Office Action dated Jul. 5, 2012, 11 pages.
In the US Patent and Trademark Office U.S. Appl. No. 12/889,697 Non-Final Office Action dated Feb. 28, 2012, 10 pages.

* cited by examiner

DATA MANAGEMENT APPARATUS FOR COMPARING PATIENT DATA WITH AILMENT ARCHETYPES TO DETERMINE CORRELATION WITH ESTABLISHED AILMENT BIOMARKERS

CROSS-REFERENCE TO RELATED APPLICATIONS

This application is a continuation-in-part of U.S. patent application Ser. No. 12/567,249 filed on Sep. 29, 2009, which application is a continuation-in-part of U.S. patent application Ser. No. 12/505,185 filed on Jul. 17, 2009. This application is also related to an application filed concurrently herewith titled "Medical Apparatus For Collecting Patient Electroencephalogram (EEG) Data" and an application filed concurrently herewith titled "Patient Data Management Apparatus For Comparing Patient EEG Data With Ailment Archetypes To Determine Correlation With Established Ailment Biomarkers." The foregoing applications are hereby incorporated by reference to the same extent as though fully disclosed herein.

FIELD OF THE INVENTION

This invention relates to medical data processing systems and, in particular, to a system that enables a physician to implement a patient-specific medical diagnostic tool which uses known sets of medical and/or psychological data, which are correlated with patient data, to identify potential patient ailments or conditions.

BACKGROUND OF THE INVENTION

There are numerous existing medical test and analysis systems, many of which are ailment-specific, for either generating patient test data for manual review by a treating physician or for analyzing collected patient test data to determine whether the patient suffers from a certain ailment or condition. These existing test and analysis systems are ailment-specific and simply process the collected patient data to provide the treating physician with a presentation of the data which can be interpreted by the treating physician to determine whether the patient suffers from the condition the test is designed to detect and/or whether the patient falls into pre-defined relevant risk groups.

Some of the latest generations of medical devices have transitioned from basic physiological measurement (that requires a trained interpretation) to a formal ailment diagnosis. The deterministic approach of these medical devices appropriately requires significant regulatory oversight to ensure the reliability and validity of the technology and the accuracy of the formal ailment diagnosis. While these objective diagnoses produced by the medical devices represent significant commercial value, they come at significant cost with respect to time and costs of empirical clinical trials, including the risk of future contradictory or displacing research. In the case of a conflict between commercial diagnostics and new research, the community of diagnosticians is left with a less than optimal solution and often is presented with a profound uncertainty resulting in a stalled decision in patient point-of-care situations. In the end, rapid change in the associated medical science can produce paralysis when physicians suspect the automated ailment diagnoses are using outdated informational and analysis sources.

A problem with physician diagnosis of ailments is that the validity of the results obtained by using this process is predicated on the treating physician both having sufficient knowledge of the ailment and also being able to identify anomalies in the patient test data, which anomalies can be subtle indicators. Medical schools are traditionally responsible for training physicians on the diagnostic utility of physiological measurements, with more training required for measures that don't have a simple FDA-approved binary solution. This education rightfully focuses on historic studies that provide the interpretation of medical device and laboratory data. These interpretations rely on the integrity and transparency of peer-reviewed scientific journals and medical texts from which a physician would base their diagnostic and treatment decisions. The primary source for these materials (both in medical school and for practicing physicians) is public and private medical libraries, each of which supports a standard for the peer review and medical validity of their content. Research on new medical devices and diagnostic interpretation are added to these libraries daily, representing an explosion in the amount of scientific studies potentially relevant to physicians' patient populations. Unfortunately for the general practitioners (and even specialists), the volume of new research is difficult to assimilate into the point-of-care without the context of a given patient measurement, and these results are often contradictory. Understanding that the ability to aggregate and interpret a variety of patient diagnostic measurements is the responsibility of the physician; however, there is a limit to the amount of raw data these highly trained professionals can integrate. Furthermore, there are little known ailments that manifest themselves in a manner that closely mimic other ailments, thereby making it difficult to diagnose these ailments, since the physician only sees patient symptoms and patient-specific test results.

A further problem is that there is a limitation in this process in that a human can only process a certain limited amount of data; and the treating physician, no matter how skilled, can fail to identify the convergence of a number of trends in the patient test data or a collection of seemingly unrelated anomalies. This is especially true when there are a number of existing patient-specific test results, such as: past ailment-specific test results, present ailment-specific test results, test results directed to test for other ailments, patient demographic and physical data, including the patient's history of medications, and the like.

A further problem derives from the fact that 21st century medicine increasingly utilizes Electronic Medical Records (EMRs) in patient care. An Electronic Medical Record is a computerized legal medical record, which is part of a localized health information system that allows organized storage, retrieval, and manipulation of information. The American Recovery and Reinvestment Act of 2009 identifies three important goals in the deployment of Electronic Medical Records: (1) improved efficiency in insurance payments, (2) reductions in duplicate testing, and (3) "to guide medical decisions at the time and place of care".

In the past, the Food and Drug Administration has not actively regulated Electronic Medical Records. However, due to the advent of new, more powerful data storing and organizing network systems that can aggregate many thousands of often anonymized records, Electronic Medical Records will soon be capable of creating hitherto nonexistent clinical databases. The problem arises when those databases begin to be used to guide medical decision-making regarding the treatment received by many patients at the time and place of care. As such, the validity of that guidance becomes a major issue of contention for the Food and Drug Administration, whose mandate is to assess the safety and effectiveness of all registered medical devices.

Naturally, a major debate has opened up regarding the question of regulatory oversight; namely, the identity of the authorities who determine the validity of the conclusions derived from the data. In the case of private corporations owning the Electronic Medical Records networks, they will not only "own" the data; they will also be incented to mine the data in such a way as to direct interpretations of it to physicians. Suspicions will certainly rise regarding the validity of these interpretations due to profit motives.

In opposition to private corporations, government agencies, including ONCHIT and the Food and Drug Administration will see the need to regulate these interpretations through the government's oversight. This process is both very slow and often uncertain and may cause harmful delays in understanding the guidance potential of the data. Furthermore, much of the data interpretation, although potentially very useful to clinical analysis at the point of care, may not meet the standard government agencies' need to certify it as effective, thereby limiting a physician's ability to utilize a potentially life-saving solution. Further problems will occur when this data begins to evolve in its interpretive guidance. As more data is collected, the guidance it provides may change very rapidly, and the government oversight process will not be able to keep up. This scenario could potentially create a confusing state of affairs between regulatory bodies and healthcare facilities.

Historically, these problems have been solved through the peer-reviewed system of scientifically researched data analysis and publication. The major benefits of this system are the constant revisions that the scientific process provides along with the self-policing effect against discredited methods that peer-reviewed publications provide. However, this process relies entirely on an open source data system that allows scientists full access to common data warehouses for independent interpretation. When that access is limited, invariably so are the results of the subsequent studies. The only flaw in this system is that the process of peer-reviewing and publication is slow; and much of the new interpretations take too long to get to the point of care, thus eliminating one of the major goals of the new Electronic Medical Records technology objectives.

Thus, there is presently no system which enables the treating physician to effectively monitor and process multiple sets of patient data and customize the analysis of this collected patient-specific data for the individual patient to cover ailments as specified by the physician (or unspecified), all in conjunction with the ability to dynamically access a Digital Library which provides the treating physician with resource materials, including control and control data sets for patients.

BRIEF SUMMARY OF THE INVENTION

The above-described problems are solved and a technical advance achieved by the present Data Management Apparatus For Comparing Patient Data With Ailment Archetypes To Determine Correlation With Established Ailment Biomarkers (termed "Patient Data Management System" herein), which enables the treating physician to monitor one or more sets of patient data and customize, using patient- or group-specific customization, the analysis of this collected patient-specific data for the individual patient to cover one or more ailments, all in conjunction with a Digital Library which provides the treating physician with resource materials, including control data sets for patients.

In this description, the term "physician" (also termed "diagnostician" or "clinician") is intended to include anyone who performs a diagnostic function, reviews data about a patient, and correlates that data with known ailments to provide the patient with a diagnosis of their present state of health. In addition, the term "ailment" (also termed "condition" herein) is used in the general sense to represent any medical or psychological or physiological condition or problem that affects, or may in the future affect, a patient, whether or not it is life- or health-threatening.

The Patient Data Management System operates under the control of a physician to implement a patient-specific instance of the apparatus which is capable of accessing at least one data manipulation module, each defining at least one process for transforming patient medical data pursuant to a predefined schema. A patient medical data processor is responsive to the physician selecting a set of patient medical data, at least one of the data manipulation modules, and an order of applying the selected data manipulation modules to the selected patient medical data for processing the selected patient medical data using the selected data manipulation modules in the selected order to identify data indicative of a predetermined condition in the selected patient medical data. A display is available for presenting a visualization of the data indicative of a predetermined condition in the selected patient medical data.

This apparatus can include a link to a Digital Library for providing access to a plurality of information sources which relate to interpreting patient medical data and possible ailments associated with patient medical data, as well as data characterization modules for calculating control variations of a set of patient medical data collected from and about an identified patient, with patient medical data of a base set of control data to identify anomalies in a set of patient medical data.

Furthermore, the Patient Data Management System can include a Digital Library interface module, which responds to receipt of the set of patient medical data collected from and about an identified patient as well as identified anomalies calculated by the data characterization module relating to the set of patient medical data, by searching the Digital Library with physician-defined search criteria to locate information sources relating to the set of patient medical data and interpretations of the identified anomalies calculated by the data characterization module relating to the set of patient medical data. An information access module provides an authorized physician with access to the information sources returned by the Digital Library interface module and relating to the set of patient medical data.

The Patient Data Management System can also access shared databases which serve a group of physicians and health care facilities to enable the physician to retrieve multiple sets of patient data as well as to accumulate point-of-care knowledge in a quickly-expanding medical-discovery environment. The physician not only can interpret medical data to provide an improved diagnosis of existing and/or future ailments by accessing the Digital Library, but also can put this data back into the system for further analysis. The patient-specific data can be configured into a patient anonymous form for this purpose to enable other physicians to benefit from the data without infringing on the privacy of the patient. The Patient Data Management System thereby creates a medical-advancement environment—the library takes patient/physician data from multiple sources including outcomes, incorporates all of the data into new knowledge, and puts the information back to the physician at a point-of-care locus.

An additional benefit of the Patient Data Management System is that the discovery of an outcome need not be linked to a predetermined physician-defined hypothesis—all the data is parameterized, and the parameters are allowed to "wander", where parameters are tested as correlations against the existing environment of all known medical outcomes. In this paradigm, the successful correlations survive as new medical discoveries which couple symptoms and/or anomalies and/or test data to an ailment. This is especially pertinent in the situation where little-known ailments are present and the physician-defined hypothesis could inadvertently exclude these little-known ailments due to the physician unknowingly biasing the analysis.

Thus, the Patient Data Management System provides diagnostic capabilities heretofore unknown in the medical profession by linking a Digital Library to the physician and patient-specific data as defined and moderated by the physician.

DETAILED DESCRIPTION OF THE INVENTION

Figure 1:
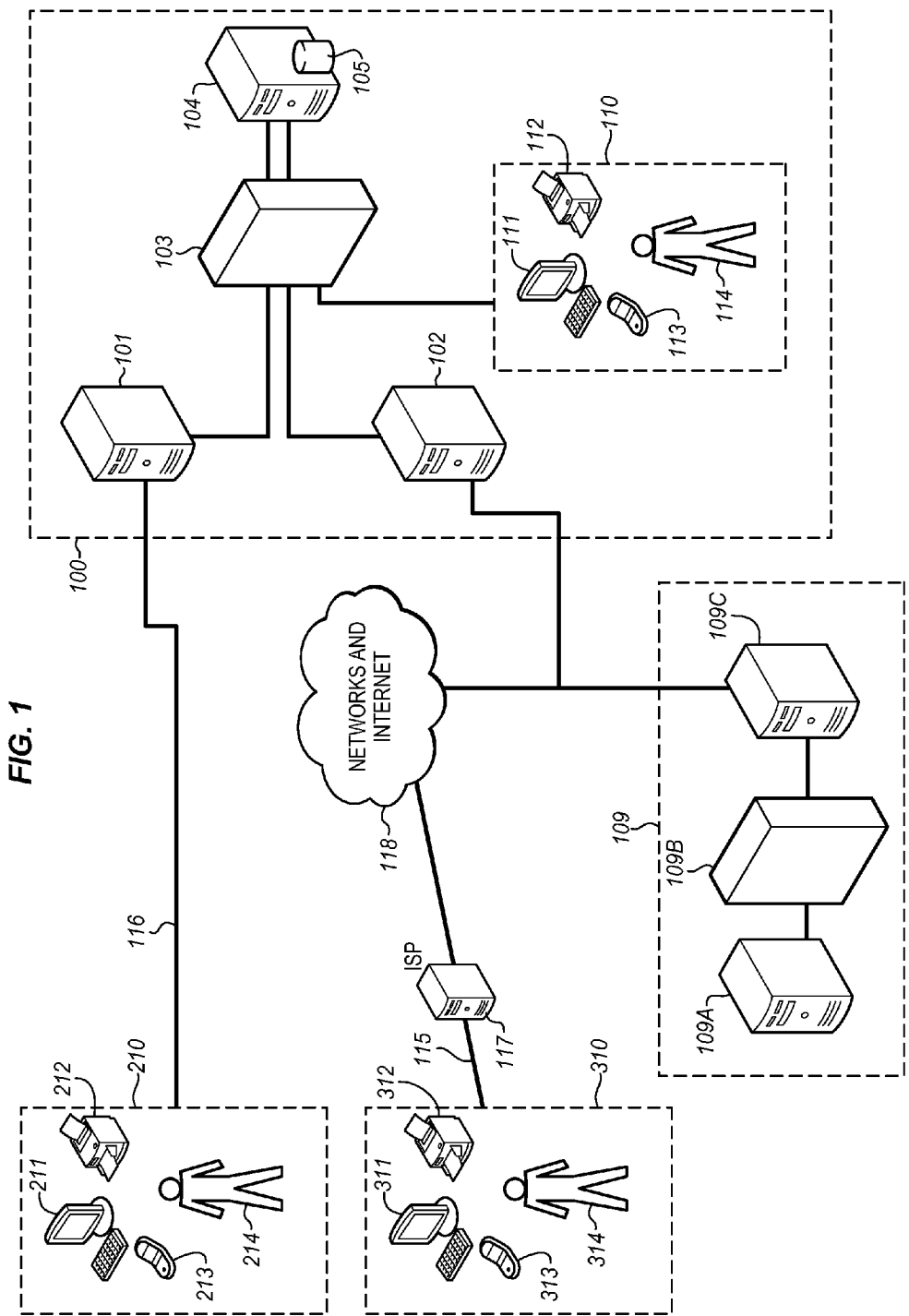
FIG. 1 is a block diagram of the present Patient Data Management System and an environment in which it is operational.

The Patient Data Management System operates under the control of a physician to implement a patient-specific instance of the apparatus which is capable of accessing at least one data manipulation module, each defining at least one process for transforming patient medical data pursuant to a predefined schema. A patient medical data processor is responsive to the physician selecting a set of patient medical data, at least one of the data manipulation modules, and an order of applying the selected data manipulation modules to the selected patient medical data for processing the selected patient medical data using the selected data manipulation modules in the selected order to identify data indicative of a predetermined condition in the selected patient medical data. A display is available for presenting a visualization of the data indicative of a predetermined condition in the selected patient medical data.

Based upon this statistical analysis, a Digital Library interface module searches the Digital Library for information sources relating to the set of patient medical data and interpretations of the identified anomalies. There can also be an information access module which provides an authorized person, such as a physician, with access to the information sources returned by the Digital Library interface module and relating to this set of patient medical data. The physician can use this information at the point-of-care on an identified patent according to the level of automation built by that physician.

In this manner, the physician's diagnosis of a patient ailment is data driven rather than physician-diagnosis driven. The collected data relating to a patient can be mapped to biomarkers selected by the physician to determine a closeness of match with the physician-selected biomarkers. In this manner, the physician can look for analogous patterns of data which are indicative of an ailment with which the patient is afflicted. The associated information sources then can be retrieved from the Digital Library by the physician to provide in-depth ailment and treatment information. This enables a physician to abandon the traditional path of selecting a diagnosis based on vague patient symptoms and then prescribing a treatment. If the treatment relieves the patient's symptoms, then the treatment is deemed successful. However, there is no positive determination that the ailment is properly identified or the treatment is the proper one for the underlying ailment. This is the weakness of traditional medical care, especially when the physician is faced with an atypical ailment, which the physician may never have previously encountered. By driving the diagnosis using the collected patient data, the physician is empowered to consider a wide variety of possible ailments without having to expend excessive time, order extensive diagnostic tests, or repeatedly cycle through successive unsuccessful treatments.

System Architecture—Patient Data Management System Communication Environment

Figure 2:
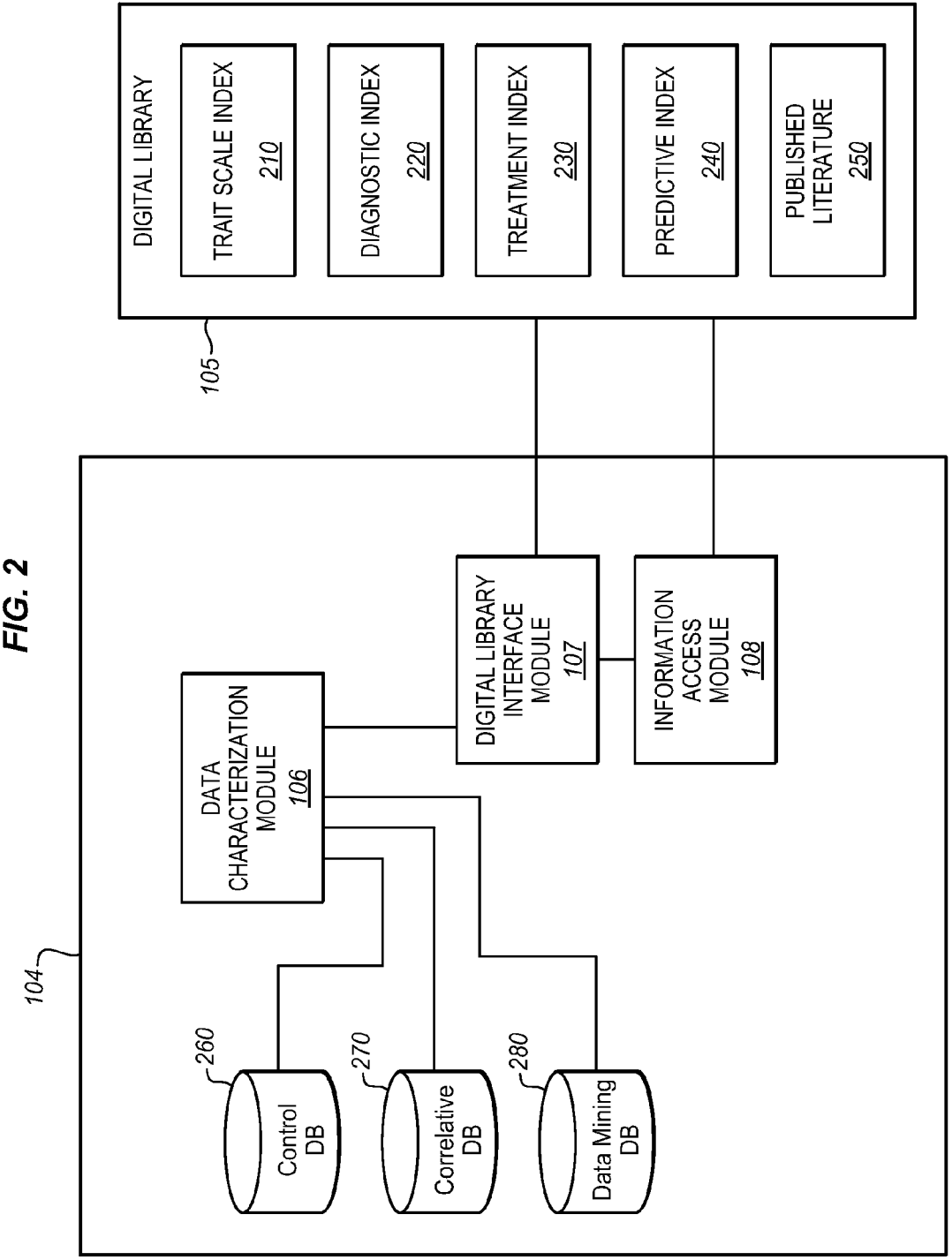
FIG. 2 is a block diagram illustrating the components of the Digital Library.

FIGS. 1 and 2 are block diagrams of the present Patient Data Management System and an environment (described in more detail in co-pending U.S. patent application Ser. No. 12/505,185) in which the present Patient Data Management System is typically operational. In particular, the communications environment is adaptable; and a physician 314 who is equipped with at least one electronic device (such as computer 311, printer/fax/scanner 312, cell phone 313, and the like—collectively termed "physician equipment 310") can be connected via a communication medium 115 (such as wire line, cable television, satellite, cellular, and the like) to an Internet Service Provider (ISP) 117 which interconnects the physician with a data communication network 118 (termed "Internet" herein) and thence to the Patient Data Management System 100. Alternatively, physician 214 who is equipped with at least one electronic device (such as computer 211, printer/fax/scanner 212, cell phone 213, and the like—collectively termed "physician equipment 210") can be directly connected via a communication medium 116 (such as wire line, cable television, satellite, cellular, and the like) to the Patient Data Management System 100. A final configuration is physician 114 who is equipped with at least one electronic device (such as computer 111, printer/fax/scanner 112, cell phone 113, and the like—collectively termed "physician equipment 110") is directly connected "on-site" to the Patient Data Management System 100. These configurations are exemplary, and the following description is directed to the functionality provided by the Patient Data Management System 100 which operates independent of the access architecture which is used.

Patient Data Management System

The Patient Data Management System 100 operates one or more Database Servers 104 to provide a secure environment for the storage and processing of data associated with the applications described herein. The Database Servers 104 (also referred to as "databases") can be implemented by a cluster of servers and interface with the Digital Library 105 which serves to store mass quantities of medical information as described below. A Firewall 103 is also provided to prevent access to the Database Server 104 except for the authorized applications. The interface server 101 and the WEB server 102 respond to requests from browsers and process the request and store and retrieve data on the associated Database Server 104 as required.

The Patient Data Management System 100 includes a Digital Library 105 for providing access to a plurality of information sources which relate to interpreting patient medical data and possible ailments associated with patient medical data, as well as a Data Characterization Module 106 for calculating control variations of a set of patient medical data collected from and about an identified patient with patient medical data of a base set of control data to identify anomalies in a set of patient medical data. Furthermore, the Database Servers 104 include a Digital Library Interface Module 107, which responds to receipt of the set of patient medical data collected from and about an identified patient as well as identified anomalies calculated by the Data Characterization Module 106 relating to the set of patient medical data, by searching the Digital Library 105 for information sources relating to the set of patient medical data and interpretations of the identified anomalies calculated by the Data Characterization Module 106 relating to the set of patient medical data. The Digital Library Interface Module 107 also contains physician selected bio-markers, ailment characteristics, search criteria, and rules engines that highlight conditions of particular concern to the physician. An Information Access Module 108 provides an authorized physician with access to the information sources returned by the Digital Library Interface Module 107 and relating to the set of patient medical data.

In addition to Digital Library 105, the physician can have access to shared medical records which reside on Medical Record Database 109, which may be part of Patient Data Management System 100 or managed as a separate entity. The Medical Record Database 109 can be a database shared among a plurality of physicians and health care facilities which serve a region or patient population. As is the norm, access to the Patient Data Management System 100 and Medical Records Database 109 is regulated to admit only authorized personnel via a secure access protocol as is known in the art. The Medical Records Database 109 includes a WEB server 109C, a Firewall 109B, and the Records Database 109A.

Database Server

Database Server 104, as shown in block diagram form in FIG. 2, consists of the processing engine which executes the processes described herein and which manages access to the Digital Library 105 and the various databases 260-280. In this regard, Control Database 260 contains control (typically normal) data sets for subject data, where the control group can be a normal control or an ailment-specific control also which both make up what is referred to as archetypal datasets. This data comprises sets of data which represent the control measurement data of various characteristics of subjects that are taken from readings on various subjects, with the data typically being parsed by subject category and subject characteristics as is well known in the art. Correlative Database 270 consists of the results of correlating patient-specific data with selected data sets contained in the Control Database 260. The correlation data represents detected anomalies which can be used by the treating physician to identify one or more ailments which affect the patient. This correlation data can be tied to a resultant diagnosis and treatment methodology (with follow-up data indicative of results or successive correlation results) and can be shared among physicians to enable other physicians to benefit from these results. The patient data is anonymized to ensure privacy of the patient, with typically only the relevant patient physical, socioeconomic, psychological, and demographic data being tied to the results. Data Mining Database 280 consists of the analysis data which are generated by physicians using the Patient Data Management System 100 and represent the results of data and literature analysis operations, including past searches and analyses performed by physicians. The Data Mining data, therefore, is the log of experiential information that is shared on a peer-to-peer basis by the physicians who access the Customized Medical Diagnostic Apparatus 100.

Thus, there are two aspects of the Patient Data Management System 100 which should be noted here. The first aspect is the patient-agnostic repository of relevant published literature 250 and indices 210-240 stored in the Digital Library 105, which are representative of the resources available to the physicians to use in their various diagnostic processes as well as for their general professional education. The second aspect of the Patient Data Management System 100 is the sets of data stored in the databases 260-280, representative of physician-generated and controlled information which is either patient-specific or control in nature. The physician generates the search strategies, analysis tools, correlation steps, and data mining operations to produce a patient-specific analysis, treatment, and ongoing care management regimen. Thus, this second aspect is representative of both physician-specific and peer-to-peer research and analysis results which collectively enhance the knowledge set available to the physicians who use the Patient Data Management System 100 in their practices.

Digital Library

The Digital Library 105 contains digitized information (Published Literature 250) such as books, scientific research, manuscripts, videos, audio files, etc., that can be used by the physician to research ailments, conditions, and other related information. The Digital Library 105 can also include a plurality of indices, such as: a Trait Scale Index 210, a Diagnostic Index 220, a Treatment Index 230, and/or a Predictive Index 240 that can aid a physician in explaining possible interpretations of patient data and making improved diagnoses. These indices contain data relations, such as the biomarkers described below, that enable the physician to statistically compare patient-specific test results to a base group of control subjects to obtain correlation data which indicate the probability of the presence of a particular psychological or physiological ailment or condition in the patient.

Trait Scale Index 210 is a collection of data relations and possibly distributions of those data relations as found in members of the control database that have been identified from literature. Diagnostic Index 220 is a set of data relations that have been correlated with diagnoses from a physician. These correlations are developed based on data accessed through the aggregated patient database stored in Data Mining Database 270. Diagnostic Index 220 may also include distributions of the data relations and may also be computed information of control subject data found in Control Database 260. Out-of-variance data relations found during the statistical analysis can be searched for in Diagnostic Index 220 in order to aid a physician in determining the ailment of a patient. Treatment Index 230 is a collection of data relating to treatments which have proven effective for patients with similar statistical characterizations of the collected patient data. Predictive Index 240 includes a set of data relations that have been correlated between earlier collected patient data and a current diagnosis from a physician. For example, a patient may go to a physician and have routine medical tests performed throughout his lifetime. In his seventies, he takes a medical test and is diagnosed with Alzheimer's. Predictive Index 240 is created by generating correlations between this and other patients' earlier test data and the current diagnosis of Alzheimer's to find early indicators.

Digital Library 105 has access to multiple publications or other types of Published Literature 250 relating to interpreting medical data and possible ailments associated with medical data. Examples of the types of publications and published information stored in or accessible to the Digital Library include, but are not limited to: books, scientific research articles, scientific research manuscripts, videos, audio files, tables, and/or summaries of published information, desk references, and the like.

Digital Library 105 can also store Physician Applications which can be loaded directly into the digital terminals used by a physician as is described below. For example, a specialist in the field of depression could create a Physician Application that has data relations the specialist would be interested in using during the statistical characterization of the relevant patient data.

Data Characterization Module

Data Characterization Module 106 is a process which typically executes on the Database Server 104 and which calculates control variations of a set of patient medical data collected from and about an identified patient with patient medical data of a base set of control data to identify anomalies in a set of patient medical data.

Digital Library Interface Module

Digital Library Interface Module 107 is a process which typically executes on the Database Server 104 and which responds to receipt of the set of patient medical data collected from and about an identified patient as well as identified anomalies calculated by the Data Characterization Module 106 relating to the set of patient medical data, by searching the Digital Library 105 for information sources relating to the set of patient medical data and interpretations of the identified anomalies calculated by the Data Characterization Module 106 relating to the set of patient medical data.

Information Access Module

Information Access Module 108 is a process which typically executes on the Database Server 104 and which provides an authorized physician with access to the information sources returned by the Digital Library Interface Module 107 and relating to the set of patient medical data.

Physician Application

As noted above, the physicians access the Patient Data Management System 100 either via Server 101 or via WEB portal server 102. The physicians' access is typically via a Physician Application 150 (shown in FIG. 3) which executes on a physician digital terminal 111, 211, and 311. The Physician Application 150 consists of various processes which enable communication with the above-noted elements of the Patient Data Management System 100 and which enable the physician to view and generate reports and data output used in the diagnosis and treatment of the patient's ailments.

Figure 3:
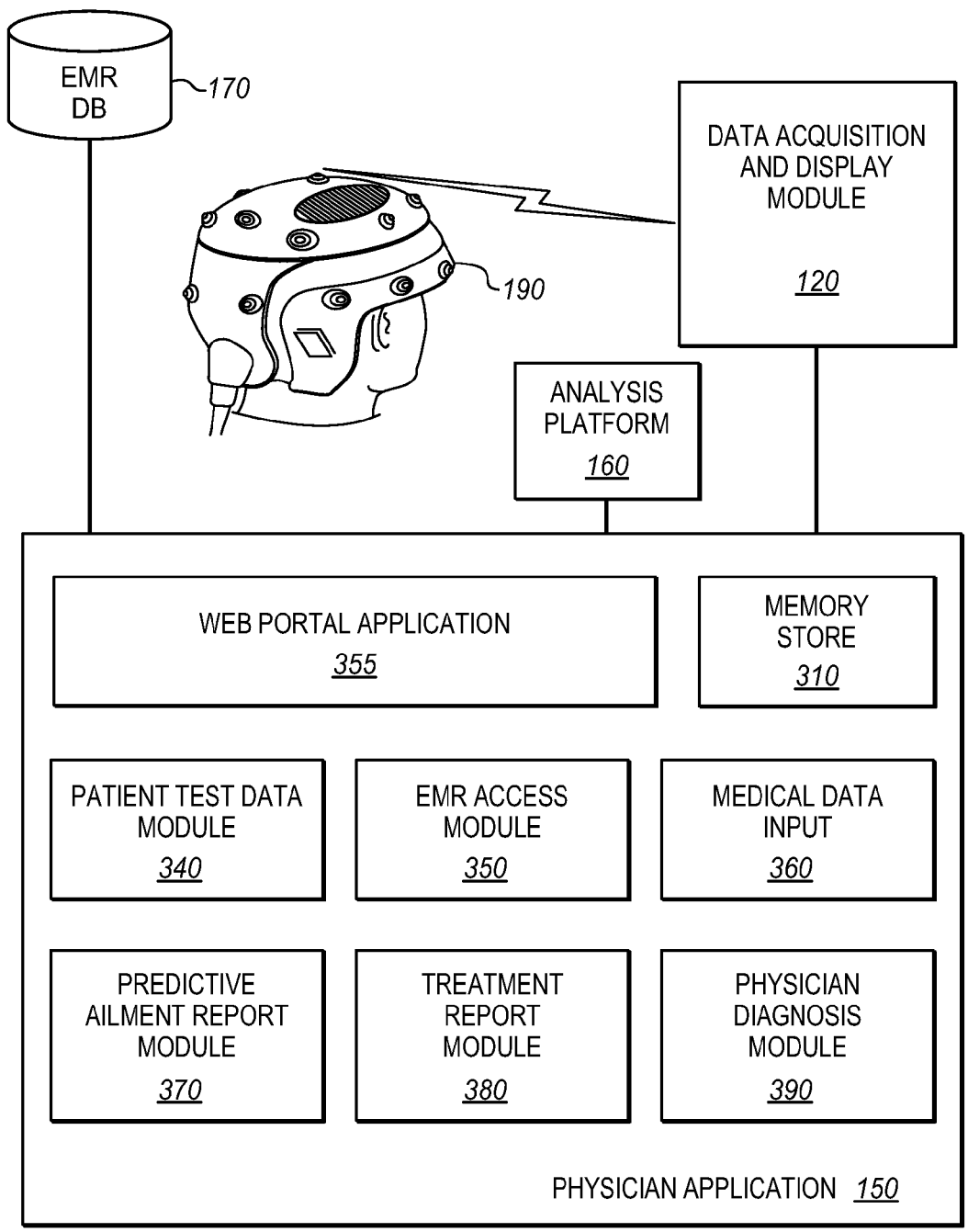
FIG. 3 is block diagram illustrating the components of the Physician Application.
Figure 5:
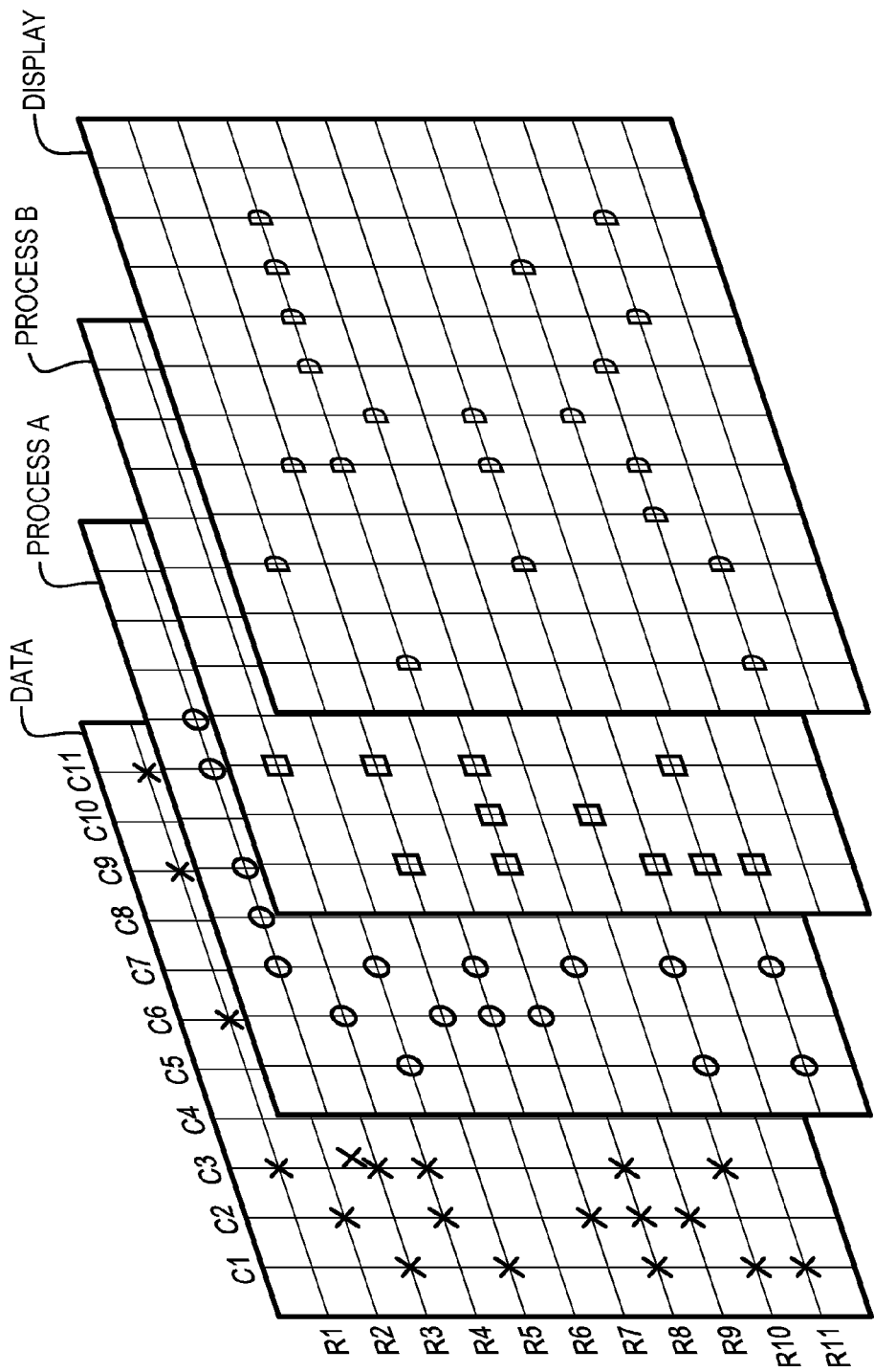
FIG. 5 illustrates the concept of selecting predetermined ailment patient data patterns.
Figure 16:
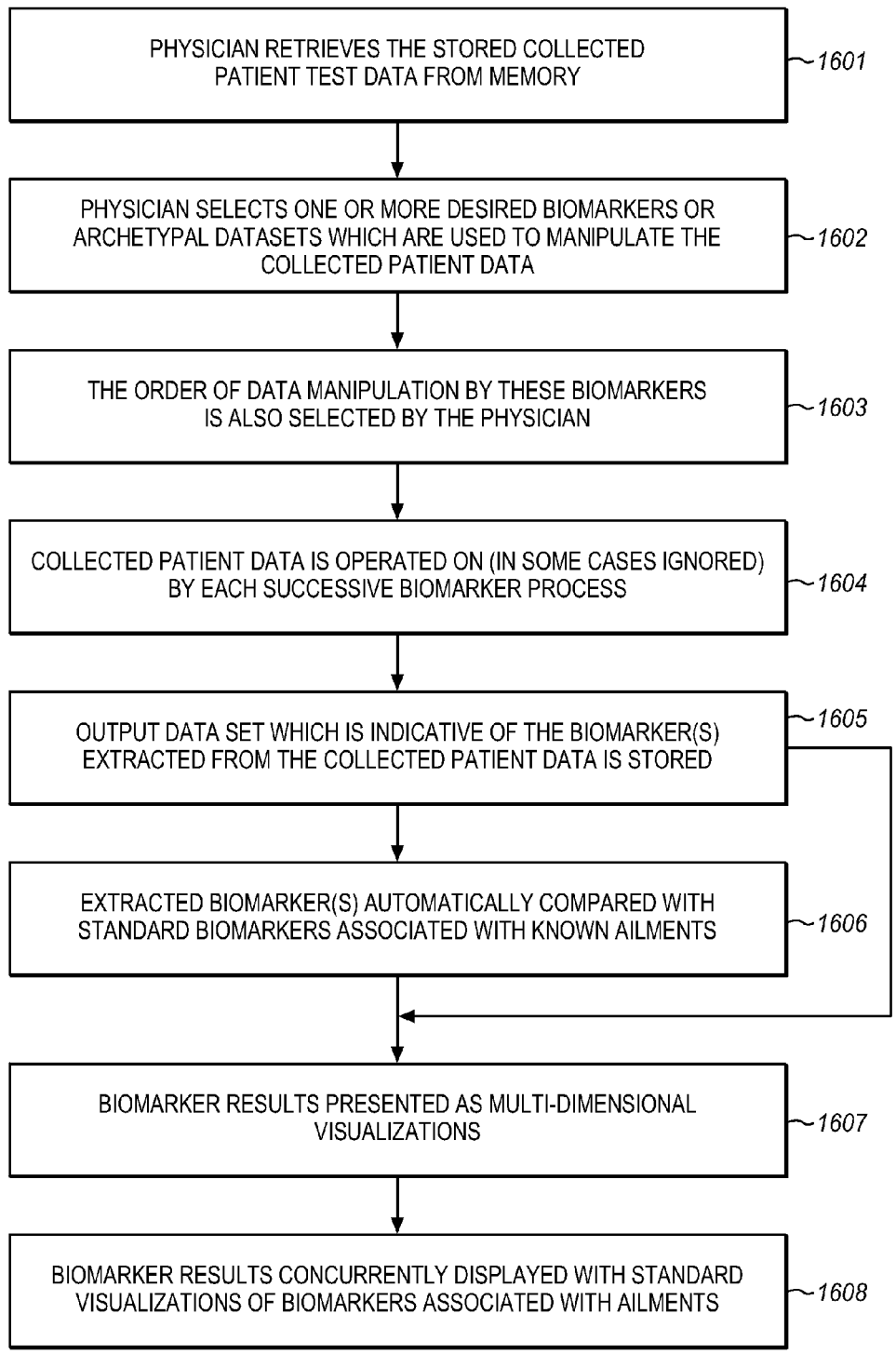
FIG. 16 illustrates in flow diagram form the operation of the Patient Data Management System.

FIG. 3 is block diagram illustrating a typical Physician Application 150 which executes an application which is part of the Patient Data Management System 100 to receive and process patient test data from and for a specific patient. The Physician Application 150 shown in FIG. 3 includes the following components which are part of Patient Data Management System 100: WEB Portal Application 335, Patient Test Data Module 340, Electronic Medical Records Access Module 350, Medical Data Input Module 360, Predicative Ailment Report Module 370, Treatment Report Module 380, and Physician Diagnosis Module 390. Memory Store 310 can have stored thereon local versions of a control database, a correlative database, a patient test database, and a data mining database. FIG. 5 illustrates the concept of selecting predetermined ailment patient data patterns, and FIG. 16 illustrates in flow diagram form the operation of the Patient Data Management System 100.

Web Portal Application 355 may be used by Physician Application 150 to connect to the Patient Data Management System 100. The Physician Application 150 can transfer patient data, such as: patient test data, data relations, medical data, and the like to the Patient Data Management System 100 and receive reports and statistical characterization results from the Patient Data Management System 100. Web Portal Application 335 is able to encrypt and decrypt the information that is being sent and received.

Patient Test Data Module 340 provides an interface between the Data Acquisition and Display Module 120 and Physician Application 150. Patient Measurement Data Module 340 also translates any requests for more patient test data from the Physician Application 150 into a format required by the Patient Data Management System 100 and translates and/or directs incoming requests and/or data to the appropriate module or application within the Physician Application 150. Patient Test Data Module 340 is a receiving module that is configured to receive sets of patient test data relating to a test subject and store the sets of patient test data in a patient test database.

Once patient test data is received through Patient Test Data Module 340, the data may be associated with sets of data received through Electronic Medical Records Access Module 350. Electronic Medical Records Access Module 350 provides an interface between Electronic Medical Records Databases 170 and Physician Application 150. Electronic Medical Records Access Module 350 translates any requests for electronic medical records from the Physician Application 150 into a format required by the destination component. Similarly, Electronic Medical Records Access Module 350 is able to translate and/or direct incoming requests (e.g., requests for passwords or other authentication) and/or data to the appropriate module or application within the Physician Application 150.

Predictive Ailment Report Module 370 and Treatment Report Module 380 interface with the Electronic Medical Records data of the patient, Storage Databases 170, and/or Analysis Platform 160 (shown in FIG. 5) to request information about current and past treatments and previously generated predictive ailment reports.

Physician Diagnosis Module 390 generates physician interface screen(s) that allow the physician to input a diagnosis. Physician Diagnosis Module 390 provides for the entry of a diagnosis, and Physician Diagnosis Module 390 can interface with the Analysis Platform 160 to retrieve a set of ailment "filters" in the form of the biomarkers described below for the physician to choose from in order to process the patient test data. If the physician likes one of those ailment filters, the physician can select it. If not, the physician is able to enter a different diagnosis through the physician interface screen options.

EEG Processing Unit

In order to illustrate the operation of the Patient Data Management System 100, the example of an EEG Processing Unit is used to demonstrate the physician's ability to selectively process collected patient data. The EEG Processing Unit is described in co-pending application titled "Medical Apparatus For Collecting Patient Electroencephalogram (EEG) Data" and comprises a semi-rigid framework which substantially conforms to the head of the Patient. The framework supports a set of electrodes in predetermined loci on the Patient's head to ensure proper electrode placement. The EEG Processing Unit includes automated connectivity determination apparatus which can use pressure-sensitive electrode placement to ensure proper contact with the Patient's scalp and also automatically verifies the electrode placement via measurements of the electrode impedance through automated impedance checking. In addition, the EEG Processing Unit can include optional automated electrode movement or rotation apparatus to clean the skin of the Patient to optimize the electrode contact with the Patient's scalp as indicated by the measured impedance.

The voltages generated by the electrodes are amplified and filtered before being transmitted to an analysis platform, which can be a Physician's laptop computer system, either wirelessly or via a set of tethering wires. The EEG Processing Unit includes an automatic artifacting capability which identifies when there is sufficient clean data compiled in the testing session. This process automatically eliminates muscle- or other physical-artifact-related voltages. Clean data, which represents real brain voltages as opposed to muscle- or physical-artifact-related voltages, thereby are produced. The automatic artifacting capability optionally includes an automatic Patient motion artifacting capability via an accelerometer that produces data indicative of Patient movement, which enhances the identification of accurate data.

Source of EEG Activity

The electrical activity of the brain can be described in spatial scales from either the currents that are generated within a single dendritic spine or the potentials that the EEG records from the Patient's scalp. Neurons, or nerve cells, are electrically active cells which are primarily responsible for carrying out the brain's functions. Neurons create action potentials, which are discrete electrical signals that travel down axons and cause the release of chemical neurotransmitters at the synapse, which is an area of near contact between two neurons. This neurotransmitter then activates a receptor in the dendrite or body of the neuron that is on the other side of the synapse, the post-synaptic neuron. The neurotransmitter, when combined with the receptor, typically causes an electrical current within the dendrite or body of the post-synaptic neuron. Thousands of post-synaptic currents from a single neuron's dendrites and body then sum up to cause the neuron to generate an action potential. This neuron then synapses on other neurons, and so on. A typical adult human EEG signal is about 10 µV to 100 µV in amplitude when measured from the scalp.

An EEG reflects correlated synaptic activity caused by post-synaptic potentials of cortical neurons. The ionic currents involved in the generation of fast action potentials may not contribute greatly to the averaged field potentials representing the EEG. More specifically, the scalp electrical potentials that produce EEGs are generally thought to be caused by the extracellular ionic currents caused by dendritic electrical activity, whereas the fields producing magneto-encephalographic signals are associated with intracellular ionic currents.

The electric potentials generated by single neurons are far too small to be picked up by an EEG. Therefore, EEG activity always reflects the summation of the synchronous activity of thousands or millions of neurons that have similar spatial orientation, radial to the scalp. Currents that are tangential to the scalp are not picked up by the EEG. Therefore, the EEG benefits from the parallel, radial arrangement of apical dendrites in the cortex. Because voltage fields fall off with the fourth power of the radius, activity from deep sources is more difficult to detect than currents near the skull.

Scalp EEG activity shows oscillations at a variety of frequencies. Several of these oscillations have characteristic frequency ranges and spatial distributions and are associated with different states of brain functioning (e.g., waking and the various sleep stages). These oscillations represent synchronized activity over a network of neurons. The neuronal networks underlying some of these oscillations are understood, while many others are not. Research that measures both EEG and neuron spiking finds the relationship between the two is complex, with the power of surface EEG only in two bands, that of gamma and delta, relating to neuron spike activity.

Clinical Use

A routine clinical EEG recording typically lasts between 20 and 30 minutes (plus preparation time) and usually involves recording from scalp electrodes which are manually placed in predetermined locations on the scalp of the Patient by the EEG test operator. A routine EEG typically is used in the following clinical circumstances, as ordered by a Physician to diagnose an Ailment and to:

distinguish epileptic seizures from other types of spells, such as psychogenic non-epileptic seizures, syncope (fainting), sub-cortical movement disorders, and migraine variants;

differentiate "organic" encephalopathy or delirium from primary psychiatric syndromes such as catatonia;

serve as an adjunct test of brain death;

prognosticate, in certain instances, in Patients with coma; and determine whether to wean Patients off anti-epileptic medications.

Additionally, EEG may be used to monitor certain procedures:

to monitor the depth of anesthesia;

as an indirect indicator of cerebral perfusion in carotid endarterectomy; and to monitor amobarbital effect during the Wada test.

An EEG also can be used in intensive care units for brain function monitoring to:

monitor for non-convulsive seizures/non-convulsive status epilepticus;

monitor the effect of sedative/anesthesia in patients in medically induced coma (for treatment of refractory seizures or increased intracranial pressure); and monitor for secondary brain damage in conditions such as subarachnoid hemorrhage (currently a research method).

In conventional scalp EEGs, the recording is obtained by the EEG test operator manually placing electrodes on the scalp with a conductive gel or paste, usually after manually preparing the scalp area by light abrasion to reduce impedance due to dead skin cells. Many systems typically use electrodes, each of which is attached to an individual wire. Some systems use caps or nets into which electrodes are embedded; this is particularly common when high-density arrays of electrodes are needed.

Electrode locations and names are specified by the International 10-20 system for most clinical and research applications and must be precisely followed by the EEG test operator in order to collect valid EEG data. This system ensures that the naming of electrodes is consistent across laboratories. In most clinical applications, 19 recording electrodes (plus ground and system reference) are used. A smaller number of electrodes are typically used when recording EEGs from neonates. Additional electrodes can be added to the standard set-up when a clinical or research application demands increased spatial resolution for a particular area of the brain.

Each electrode is connected to one input of a differential amplifier (one amplifier per pair of electrodes); a common system reference electrode is connected to the other input of each differential amplifier. These amplifiers amplify the voltage between the active electrode and the reference. In analog EEGs, the signal is then filtered, and the EEG signal is output as the deflection of pens as paper passes underneath. Most EEG systems are digital, and the amplified signal is digitized via an analog-to-digital converter, after being passed through an anti-aliasing filter. Analog-to-digital sampling typically occurs between 256 Hz and 512 Hz in clinical scalp EEGs; sampling rates of up to 20 kHz are used in some research applications.

The digital EEG signal is stored electronically and can be filtered for display. Typical settings for the high-pass filter and a low-pass filter are 0.5-1 Hz and 35-70 Hz, respectively. The high-pass filter typically filters out slow artifact, such as electrogalvanic signals and movement artifact, whereas the low-pass filter filters out high-frequency artifacts, such as electromyographic signals. An additional notch filter is typically used to remove artifact caused by electrical power lines (60 Hz in the United States and 50 Hz in many other countries).

EEG Processing Unit

Figure 6:
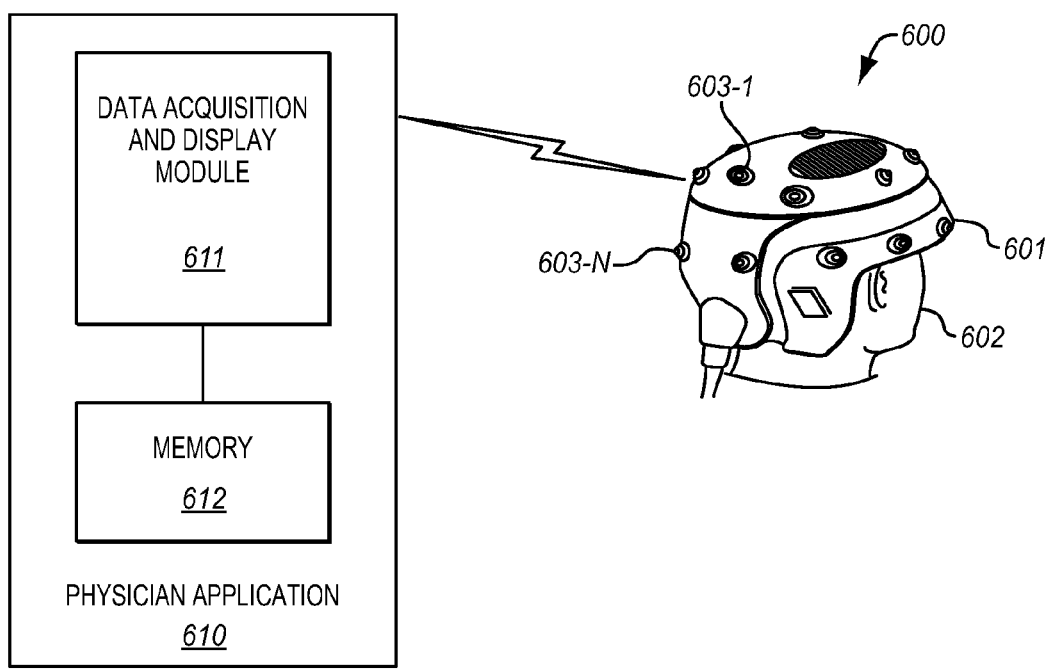
FIG. 6 is a block diagram of an EEG Processing Unit and an environment in which it is operational.

FIG. 6 is a block diagram of the present EEG Processing Unit and an environment in which it is operational. The EEG Processing Unit 600 includes "helmet-like" frame apparatus 601, which is typically semi-rigid in nature, conforms to the head of the Patient 602, and supports a set of electrodes 603-1 to 603-N, in predetermined loci, on the Patient's head to ensure proper electrode placement. Proper electrode placement is critical to the collection of accurate data to enable the Physician to obtain readings of the above-mentioned Waves and to distinguish anomalies in these Waves from normal patterns. In addition, associating electronics with the sensors in the EEG Processing Unit enables signal sampling and signal processing close to the source of the EEG signals so that the data that is transmitted for storage and review by the Physician is relatively noise-free before it leaves the EEG Processing Unit.

Figure 7:
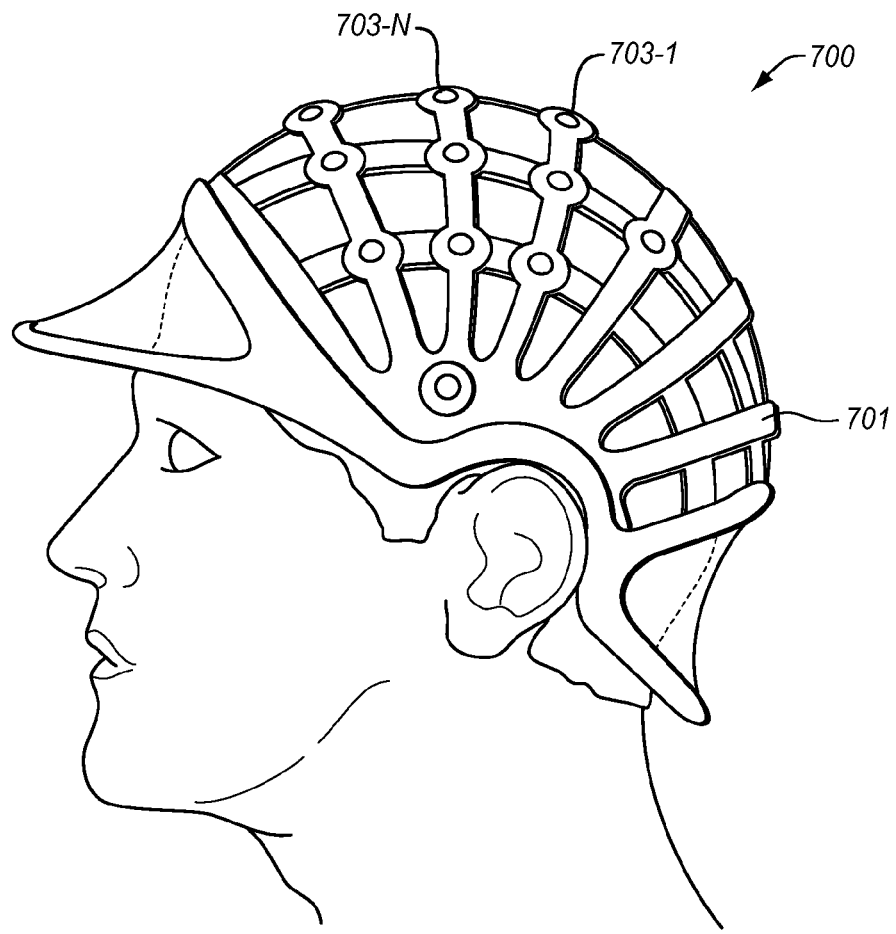
FIG. 7 is a block diagram illustrating an alternative embodiment of the EEG Processing Unit which makes use of an exoskeleton in the EEG Processing Unit.

FIG. 7 is a block diagram illustrating an alternative embodiment of the EEG Processing Unit 600 which makes use of an exoskeleton 701 as an alternative to the "helmet" 601 design shown in FIG. 6. As with the "helmet" design, the exoskeleton 701 conforms to the head of the Patient and is a semi-rigid framework which supports a set of electrodes 703-1 to 703-N, in predetermined loci, on the Patient's head to ensure proper electrode placement.

EEG Electrode Placement System

Figure 8:
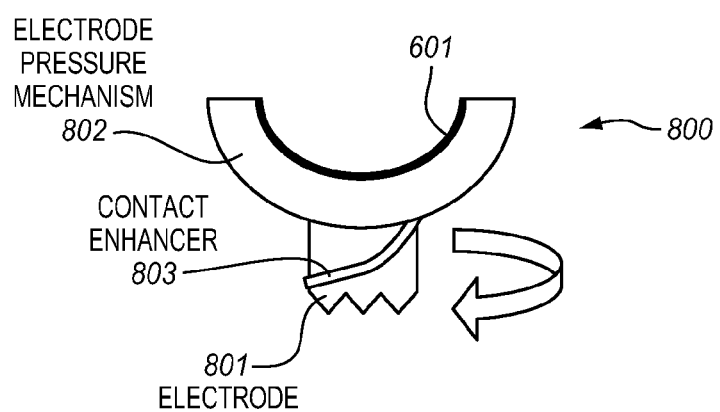
FIG. 8 is a block diagram illustrating an implementation of the EEG Transducer Placement System used in the EEG Processing Unit.

FIG. 8 is a block diagram illustrating an implementation of the EEG Electrode Placement System 800 used in the EEG Processing Unit 600. The EEG Electrodes 801 comprise sensitive electronics, as shown in additional detail in FIG. 10, which includes automated connectivity determination apparatus which uses pressure-sensitive electrode placement to ensure proper contact with the Patient's scalp and also automatically verifies the electrode placement via measurements of the electrode impedance through automated impedance checking. In particular, the EEG Transducer Placement System 800 includes an Electrode Pressure Mechanism 802 that, upon placement of the EEG Processing Unit 600 on the head of the Patient 602, is activated by the EEG test operator to apply pressure to the individual EEG Electrodes 801 which are attached to the exoskeleton 601 or 701 thereby to ensure secure contact of the EEG Electrode 801 with the scalp of the Patient 602. The Electrode Pressure Mechanism 802 consists of any of a spring mechanism, inflatable bladder(s), hydraulic plunger(s) and the like, which apply mechanical pressure to the "back side" of the EEG Electrodes 801 thereby to force them away from the interior surface of the exoskeleton 601 or 701 until the EEG Electrodes 801 come into firm contact with the scalp of the Patient 602.

Figure 10:
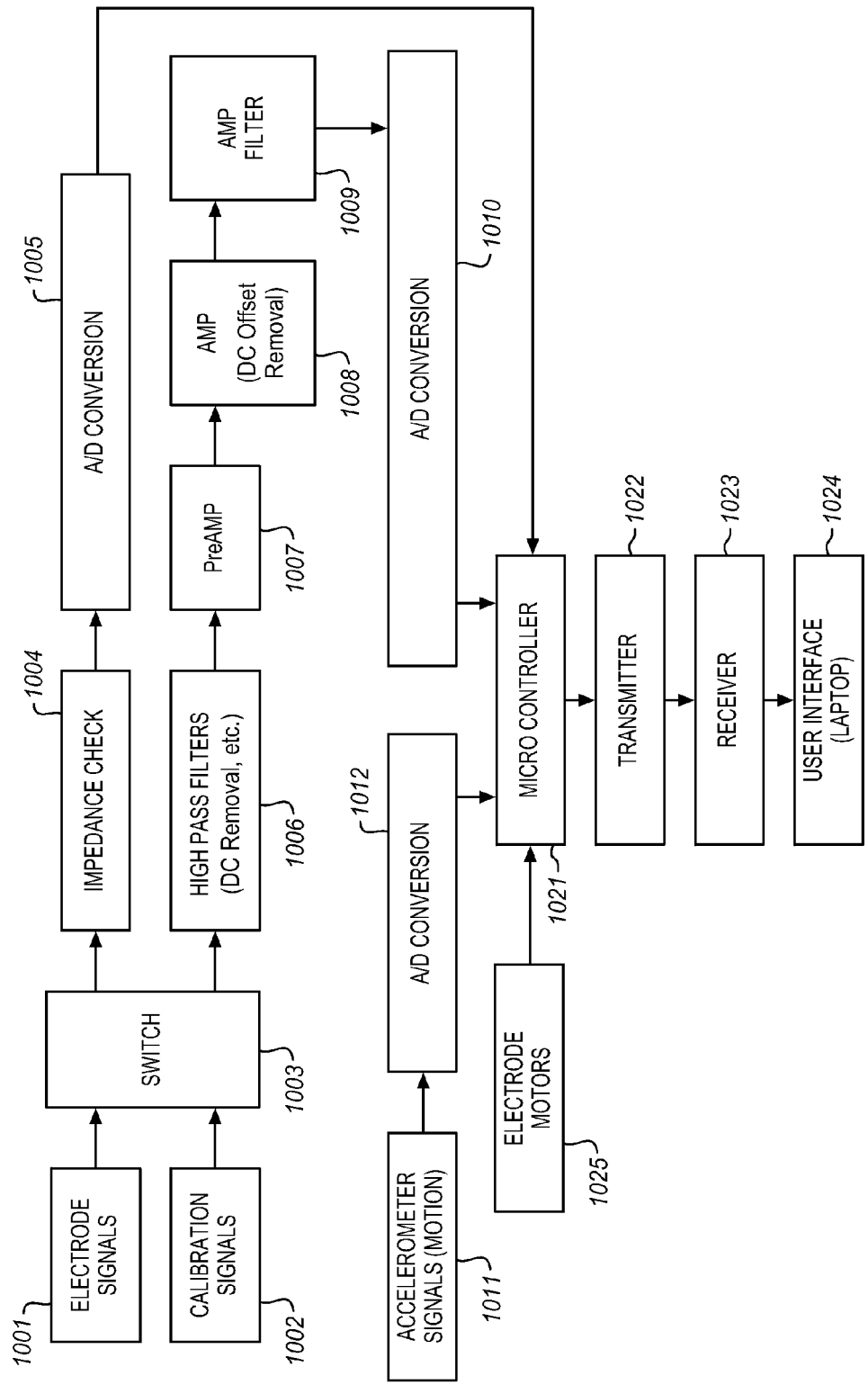
FIG. 10 illustrates a circuit diagram of the elements incorporated in the electrodes and the associated communications controller.
Figure 11:
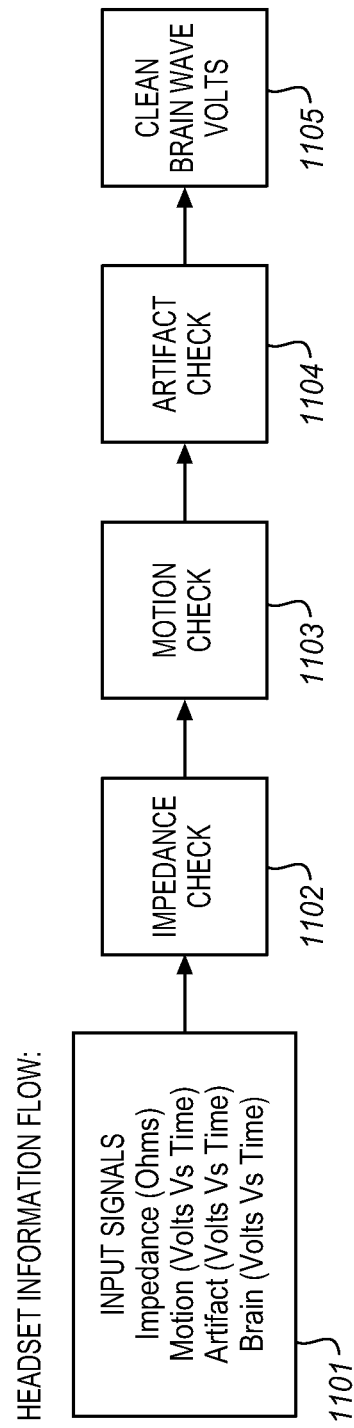
FIG. 11 illustrates in flow diagram form the operation of the processor incorporated in the electrodes.
Figure 12A:
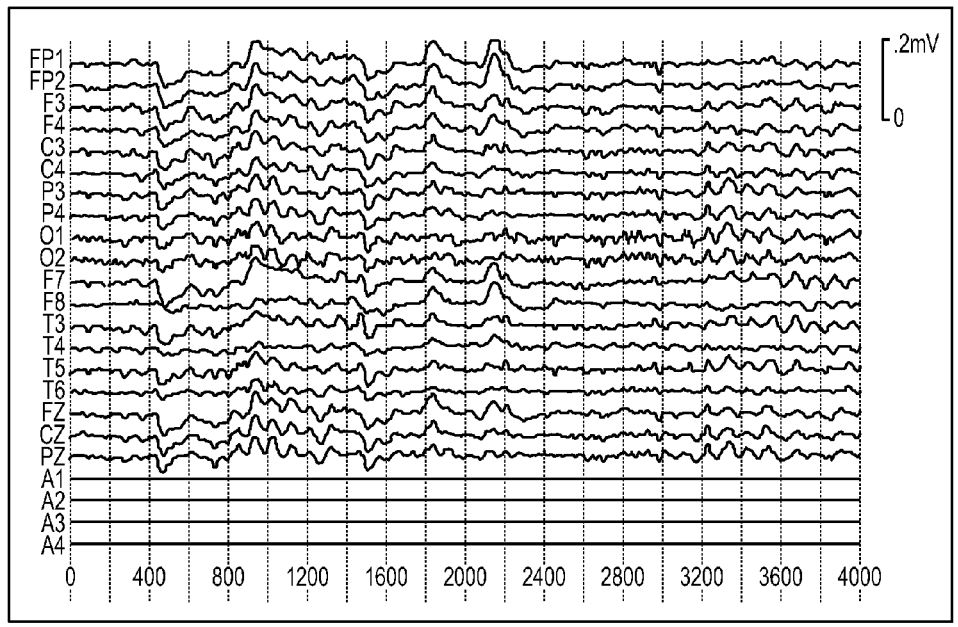
FIGS. 12A and 12B illustrate an example of EEG data that may be gathered during an EEG test.
Figure 12B:
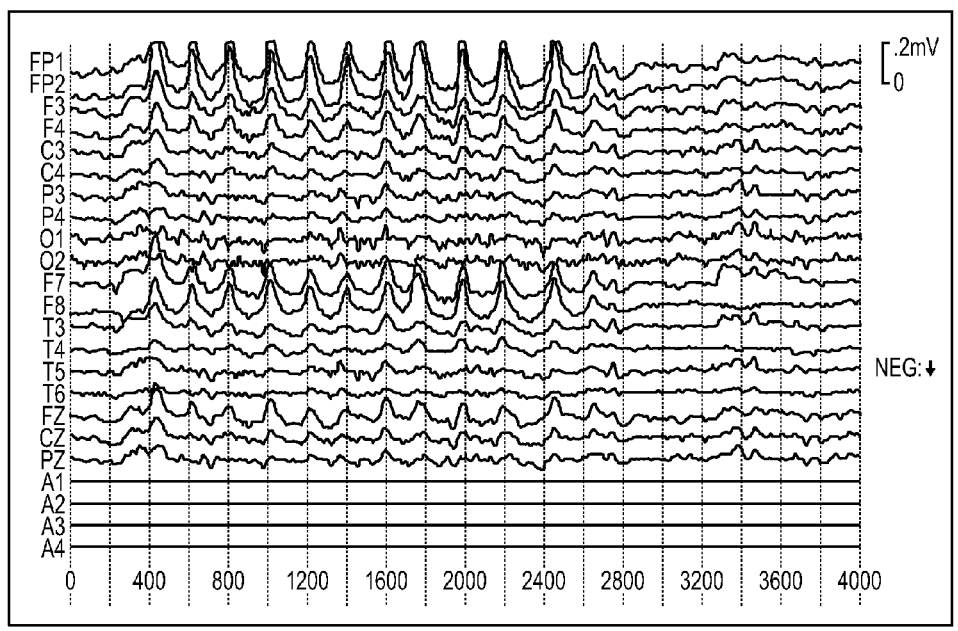

In addition, the EEG Processing Unit 600 can include optional automated Contact Enhancer Mechanism 803, which provides movement and/or rotation of the EEG Electrode 801 to clean the skin of the Patient 602 to optimize the electrode contact with the Patient's scalp as indicated by the measured impedance (described with respect to FIGS. 10 and 11).

EEG Electrode Placement

Figure 9:
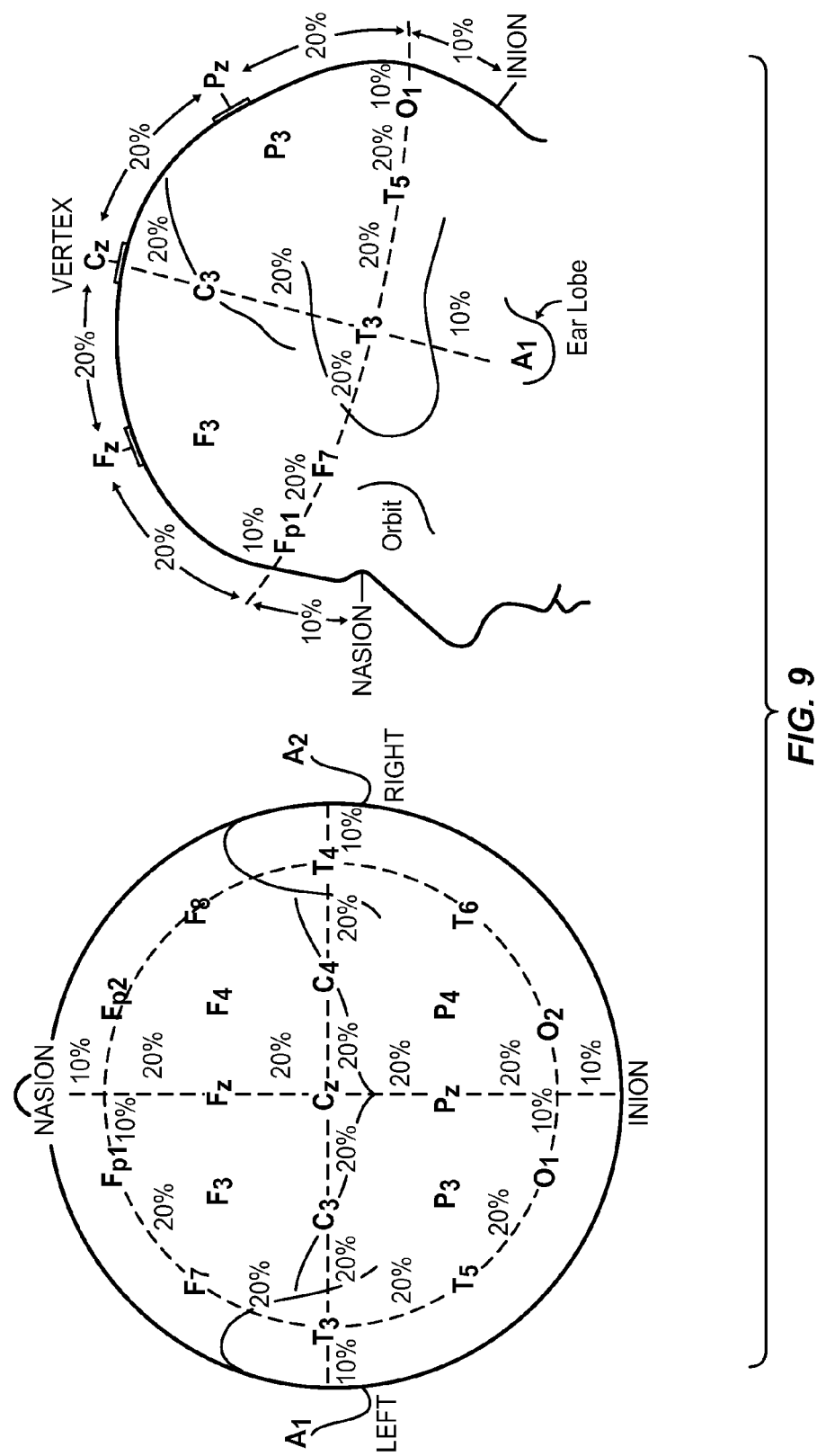
FIG. 9 is a block diagram illustrating an example electrode placement for gathering EEG data.

FIG. 9 is a block diagram illustrating an example electrode placement for gathering EEG data and represents electrode placement consistent with the International 10-20 EEG Classification System. Each electrode site has a letter to identify the lobe and a number or another letter to identify the hemisphere location. The letters C, F, Fp, O, P, and T stand for Central, Frontal, Frontal Pole, Occipital, Parietal, and Temporal locations of the brain, respectively. The even numbers refer to locations in the right hemisphere, the odd numbers refer to locations in the left hemisphere, and the letter "z" refers to an electrode placed on the midline. It is evident that, due to the number of the electrodes, the test operator must carefully associate each electrode with its predefined site on the Patient's head and ensure good physical contact of the electrode with the scalp before initiating the EEG test.

EEG Electrode

FIG. 10 illustrates a circuit diagram of the elements incorporated in the electrodes (603-1 to 603-N and 703-1 to 703-N, which are collectively denoted as EEG electrode 1000 in this Figure to describe a typical electrode) and the associated transmitter 1022.

The voltages generated by the EEG sensor 1001 contained in the EEG Electrode 1000 are amplified and filtered before being transmitted to an analysis platform, which can be a Physician's laptop, either wirelessly or via a set of tethering wires. The EEG Processing Unit 600 includes automatic artifacting which identifies when there is sufficient clean data compiled in the testing session. This process eliminates muscle or other physical artifact-related voltages. Clean data, which represents real brain voltages as opposed to muscle or physical artifact related voltages, are thereby produced. The apparatus includes automatic motion artifacting via an accelerometer that produces data which enhances the identification of accurate data.

The data collected by the sensors can be over sampled to enable a filter to effectively separate the signal from the noise. Over sampling is only performed on the pass-band information and not all of the data. One reason for over sampling only on the pass-band information is that it is not necessary to communicate all of the data but only the data in the pass-band.

In traditional applications, in which the filtering was performed after the raw data was transmitted to a remotely located processor, all of the data was over sampled and sent over the communications channel. The use of over sampling and filtering in the EEG Processing Unit 600 reduces the bandwidth requirements of the data link and results in a cost savings over traditional systems. Furthermore, this architecture results in processing data with a signal-to-noise ratio that is lower than traditional systems. Consequently, the need for the use of conductive fluid on the sensor 1001 can be reduced or even eliminated in some cases.

FIG. 10 is a block diagram illustrating the layout of various components of the EEG Electrode 1000, which includes: EEG electrode signals 1001; calibration signals 1002; switch 1003; impedance check 1004; the filters 1006, 1009; the chain of amplifiers 1007, 1008; Analog to Digital (A/D) converters 1005, 1010, 1012; optional accelerometer 1011; optional electrode motor 1025; and microcontroller 1021, all located in or proximate to EEG Electrode 1000 as shown in the Figures. The Analog-Digital Converters 1005, 1010, 1012 and the microcontroller 1021 can be part of the same electronic chip. One advantage of placing the microcontroller 1021 in the EEG Electrode 1000 assembly is that the data rate of the digital communications is kept to a minimum. In addition, the data processing task is distributed, simplifying the EEG Processing Unit 600 and, consequently, the cost.

FIG. 11 illustrates in flow diagram form the operation of the EEG Processing Unit 600. At step 1101, after the EEG Processing Unit 600 has been placed on the head of the Patient 602 and activated, the EEG Electrode 1000 generates analog electrode signals which contain multiple components: EEG signals, artifacts, and impedance measurements. The EEG voltages in electrode signals 501 can be replaced by calibration signals 502 generated by signal generators. Test waveforms are generated in software and then output as calibration signals 502, which are artificial representations of standard EEG, in both shape and voltage amplitudes, for the purpose of calibration and testing. In addition, accelerometer 511 generates motion signals indicative of the movement of the framework in three dimensions. A number of data processing steps operate on the EEG data to produce processed EEG data. In particular, at step 1102, impedance measurement device 1004 measures the impedance of the EEG sensor 1000 which is indicative of the attachment of the EEG sensor 1000 to the scalp of the Patient 102. Impedance is measured by applying a small AC voltage between each scalp electrode and the ground electrode and measuring the resultant peak-peak voltage. The results of this test are processed by A/D Converter 1005 and transmitted by the microcontroller 1021 to the user interface 1024 for display via transmitter 1022 and receiver 1023 to enable the test operator to determine whether to proceed with the data collection process or readjust the EEG sensors 1000. Alternatively, an automated electrode fit process can be executed, where the impedance values are fed to the microcontroller 1021, which forwards these values (or other control signals) to the associated electrode positioning motors 1025. The electrode positioning motor voltage and/or current readings are returned to the microcontroller 1021; and if the measured impedance value was low, the electrode positioning motor 1025 (a servo or stepping type of motor) moves to reposition the electrode on the scalp. The adjustment cycle continues until the specified impedance value is reached. Alternatively, inward motion of the electrode onto the scalp creates pressure; and the sensed electrode positioning motor drive current or voltage is monitored until the pressure cutoff value is reached, as indicated by the measured electrode positioning motor drive current or voltage.

At step 1103, the presence of motion is determined by accelerometer 1011 generating signals indicative of three-dimensional motion. The accelerometer 1011 output is processed by A/D Converter 1012 and transmitted by the microcontroller 1021 to the user interface 1024 for display via transmitter 1022 and receiver 1023 to enable the test operator to determine whether to proceed with the data collection process or readjust the EEG sensors 1001.

At step 1104, artifacts in the EEG data are processed by transmitting these analog signals via switch 1003 to high pass filter 1006 to remove DC components of the EEG data and out-of-band signals. Pre-Amplifier 1007 and Amplifier 1008 increase the magnitude of the EEG data signals, and these then are filtered by Amplifier Filter 1009 before being converted to DC signals by A/D Converter 1010. This processing is supplemented by software in microcontroller 1021 where the EEG data then is processed by artifact-removal software to remove artifacts (e.g., electrical signals from muscle movement) to ensure that proper data was collected. Artifact detection serves three purposes: the first is to allow the administrator to instruct the patient when muscle-related artifacts are overwhelming the signal (for example, excessive eye movement or muscle tension); the second is to inform the administrator when enough clean data has been obtained and test is complete; and the third is for post-hoc data analysis which may include identification of clean epics or the cleaning of contaminated epics. The microcontroller 1021 automatically determines whether the data is of adequate quality for transmission to the user interface 1024 for display via transmitter 1022 and receiver 1023. The processed EEG data 1105 (clean brain wave voltages) then is received by the Physician Application 610 where it is stored in memory 612 for later display by the Physician for analysis and diagnosis.

In response to receiving sets of EEG data relating to a Patient, a data selection physician interface screen can be displayed that allows the Physician to select a desired data manipulation process to use on the collected data as illustrated diagrammatically in FIG. 5. In some cases, the data selection physician interface screen allows the Physician to select a portion of the data collected which is analyzed and/or displayed. For example, if a large amount of EEG data is collected under a variety of test conditions, the Physician could select the portion of the EEG data for analysis that is desired by the Physician.

Steps To Create A Patient/Condition Database

In order to have a baseline reference for manipulating the Patient data collected as part of a test, such as the EEG test described above, there must be a statistically valid compilation of relevant patent data which can be used to identify conditions/ailments. This compilation is generated by collecting reference data (referred to as control database in FIG. 2) on 'N' conditions for M>>1 patients per condition. Conditions can include ailments, ailment risks, performance categories, behavior categories, intervention categories, single or multiple device or physiological test results, and/or individual patient identification. The data can include EEG data placed into a voltage vs. time matrix, with the number of dimensions being the number of EEG channels. For example, as noted above, EEG voltage readings can be collected from 19 scalp sites, sampled at 120 Hz for 100 sec, on a number of patients who test normal regarding brain function. These 12,000 data points from each patient can become part of a normal reference. EEG data can also be collected on patients who have been diagnosed with Alzheimer's and this becomes a second reference. EEG data can be collected on patients who had a recent concussion from an auto accident, and these become a third reference, etc.

The data collection process may include outcome-based "auto artifacting" to eliminate spurious voltage readings that are not related to brain readings. For example, the three major types of artifacts in current 19-channel EEG data sets are caused by eye movement, body movement, and neck and facial muscle tension. An additional class of artifacts may be caused by poor electrode contact or equipment malfunction. The presence of these artifacts compromises the performance of certain algorithms, as well as other methods of state discrimination. These artifacts are characterized by EEG waveforms with a typical morphology and distribution which can be detected in the frequency domain. The presence of artifacts in EEG data tends to a) reduce the ability to discriminate between EEG acquired in different states, and b) obscure similarities between data sets acquired in the same state.

To minimize the effect of the above-mentioned kinds of EEG artifacts, multichannel spectral thresholding can mark EEG file epochs as "included" or "deleted". The automated EEG artifacting algorithm may then be "re-tuned" using new objective functions, depending on the "outcome" or the targeted EEG parameters being measured. For example, a raw-wave spike analysis could require a different level of artifacting detail than a parameter derived from a spectral analysis of different frequencies such as a Fourier Transform. These artifacting techniques include Laplacian Eigenvalue techniques applied to new target data sets associated with more reliable diagnostic information, and may employ ICA and/or other signal processing techniques for more accurate artifact detection.

Data Is Compiled Into A Single Archetype Dataset For Each Condition

The collected patient data then is compiled into a single archetype dataset for each condition. The compilation may include normalization or averaging for outlier exclusion or to establish boundary values.

For example, the 12,000 data points (not necessarily time continuous) from the patient in the normal reference (above) can each be placed into 19-dimensional space, with each dimension equal to the voltage reading from a particular electrode, and placed into a voltage vs. time reference. These can be stored as a 19×12,000 matrix, where the number of rows equals the number of electrodes (only 2 columns shown for the sake of simplicity):

| Volts (time 1, channel 1) | Volts (time 2, channel 1) |
| Volts (time 1, channel 2) | Volts (time 2, channel 2) |
| ... | ... |
| Volts (time 1, channel 19) | Volts (time 2, channel 19) |

Establish Biomarker To Define Each Archetype

In order to uniquely define each archetype, biomarkers can be used. A biomarker is anything that can be used as an indicator of a particular disease state or some other biological state of an organism. Biomarkers are characteristic biological properties that can be detected and measured in parts of the body like the blood or tissue. Disease-related biomarkers give an indication of whether there is a threat of disease (risk indicator or predictive biomarkers), if a disease already exists (diagnostic biomarker), or how such a disease may develop in an individual case (prognostic biomarker). For chronic diseases, whose treatment may require patients to take medications for years, accurate diagnosis is particularly important, especially when strong side effects are expected from the treatment. In these cases, biomarkers are becoming more and more important, because they can confirm a difficult diagnosis or even make it possible in the first place. A number of diseases, such as Alzheimer's disease or rheumatoid arthritis, often begin with an early, symptom-free phase. In such symptom-free patients, there may be more or less probability of actually developing symptoms. In these cases, biomarkers help to identify high-risk individuals reliably and in a timely manner so that they can either be treated before onset of the disease or as soon as possible thereafter. Biomarkers may result from Eigenvector decomposition of the above-noted data Matrix, or statistical pattern recognition techniques can be used. Error spreads may be developed to establish boundaries for archetype definitions, since a range of values is typically necessary to define the archetype.

For example, all patients for each archetype can be placed into a single matrix. The 3 Eigenvectors of each of the 3 archetypes (noted above as examples) that are the most significant biomarkers for each archetype can be used to define the 3 of the 19 dimensions that are most significant. The data points from each of the 3 archetypes can be displayed against each other to define the biomarkers. Comparisons can be visual or as a percentage of points that match.

Eigenvectors

In mathematics, eigenvalue, eigenvector, and eigenspace are related concepts in the field of linear algebra. Eigenvalues, eigenvectors and eigenspaces are properties of a matrix. They are computed by a method described below, give important information about the matrix, and can be used in matrix factorization. In general, a matrix acts on a vector by changing both its magnitude and its direction. However, a matrix may act on certain vectors by changing only their magnitude, and leaving their direction unchanged (or possibly reversing it). These vectors are the eigenvectors of the matrix. A matrix acts on an eigenvector by multiplying its magnitude by a factor, which is positive if its direction is unchanged and negative if its direction is reversed. This factor is the eigenvalue associated with that eigenvector. An eigenspace is the set of all eigenvectors that have the same eigenvalue. The concepts cannot be formally defined without prerequisites, including an understanding of matrices, vectors, and linear transformations. The technical details are given below.

Eigenvector—Mathematical Definition

In linear algebra, there are two kinds of objects: scalars, which are just numbers; and vectors, which can be thought of as arrows, and which have both magnitude and direction (though more precisely a vector is a member of a vector space). In place of the ordinary functions of algebra, the most important functions in linear algebra are called "linear transformations"; and a linear transformation is usually given by a "matrix", an array of numbers. Thus instead of writing f(x) we write M(v) where M is a matrix and v is a vector. The rules for using a matrix to transform a vector are given in the article linear algebra.

If the action of a matrix on a (nonzero) vector changes its magnitude but not its direction, then the vector is called an eigenvector of that matrix. A vector which is "flipped" to point in the opposite direction is also considered an eigenvector. Each eigenvector is, in effect, multiplied by a scalar, called the eigenvalue corresponding to that eigenvector. The eigenspace corresponding to one eigenvalue of a given matrix is the set of all eigenvectors of the matrix with that eigenvalue.

EXAMPLE

If a matrix is a diagonal matrix, then its eigenvalues are the numbers on the diagonal and its eigenvectors are basis vectors to which those numbers refer. For example, the matrix $$\begin{bmatrix} 3 & 0 \\ 0 & 0.5 \end{bmatrix}$$

stretches every vector to three times its original length in the x-direction and shrinks every vector to half its original length in the y-direction. Eigenvectors corresponding to the eigenvalue 3 are any multiple of the basis vector [1, 0]; together they constitute the eigenspace corresponding to the eigenvalue 3. Eigenvectors corresponding to the eigenvalue 0.5 are any multiple of the basis vector [0, 1]; together they constitute the eigenspace corresponding to the eigenvalue 0.5. In contrast, any other vector, [2, 8] for example, will change direction. The angle [2, 8] makes with the x-axis has a tangent of 4, but after being transformed, [2, 8] is changed to [6, 4], and the angle that vector makes with the x-axis has a tangent of ⅔.

Linear transformations of a vector space, such as rotation, reflection, stretching, compression, shear, or any combination of these, may be visualized by the effect they produce on vectors. In other words, they are vector functions. More formally, in a vector space L, a vector function A is defined if for each vector x of L there corresponds a unique vector y=A(x) of L. For the sake of brevity, the parentheses around the vector on which the transformation is acting are often omitted. A vector function A is linear if it has the following two properties:

Additivity: $A(x+y)=Ax+Ay$

Homogeneity: $A(\alpha x)=\alpha Ax$ where x and y are any two vectors of the vector space L and α is any scalar. Such a function is variously called a linear transformation, linear operator, or linear endomorphism on the space L.

Given a linear transformation A, a non-zero vector x is defined to be an eigenvector of the transformation if it satisfies the eigenvalue equation $Ax=\lambda x$ for some scalar $\lambda$. In this situation, the scalar $\lambda$ is called an eigenvalue of A corresponding to the eigenvector x.

The key equation in this definition is the eigenvalue equation, $Ax=\lambda x$. That is to say that the vector x has the property that its direction is not changed by the transformation A, but that it is only scaled by a factor of $\lambda$. Most vectors x will not satisfy such an equation; a typical vector x changes direction when acted on by A, so that Ax is not a multiple of x. This means that only certain special vectors x are eigenvectors, and only certain special scalars $\lambda$ are eigenvalues. Of course, if A is a multiple of the identity matrix, then no vector changes direction, and all non-zero vectors are eigenvectors.

Factor Analysis

In factor analysis, the eigenvectors of a covariance matrix or correlation matrix correspond to factors, and eigenvalues correspond to the variance explained by these factors. Factor analysis is a statistical technique used to deal with large quantities of data. The objective is to explain most of the covariability among a number of observable random variables in terms of a smaller number of unobservable latent variables called factors. The observable random variables are modeled as linear combinations of the factors, plus unique variance terms. Eigenvalues are used in analysis used by Q-methodology software; factors with eigenvalues greater than 1.00 are considered significant, explaining an important amount of the variability in the data, while eigenvalues less than 1.00 are considered too weak, not explaining a significant portion of the data variability.

Physician Application Setup

Figure 4:
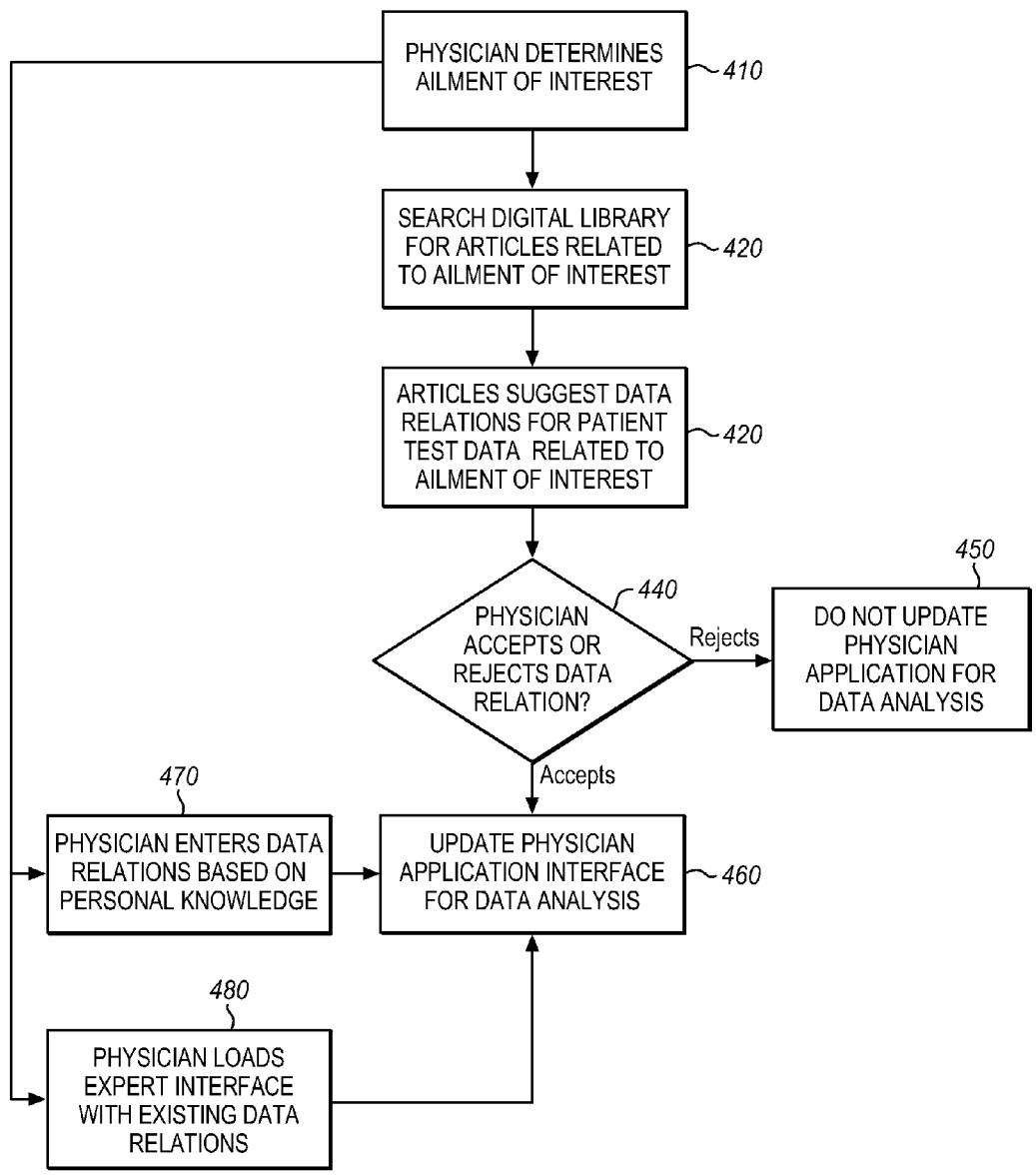
FIG. 4 is a flow chart illustrating operations for setting up or updating a Physician Application interface.

FIG. 4 is a flow chart illustrating operations for setting up or updating a Physician Application 150. In FIG. 4, a physician first determines a potential ailment or condition of interest at step 410. For example, when a patient arrives at a physician's office, the physician can make an initial assessment of the patient and determine that the patient may have a certain ailment or condition (e.g., depression). In other situations, the physician could have decided that he wants to screen all his patients for a certain ailment (e.g., attention deficit disorder). Still yet, selections of certain ailments could occur automatically. For example, the physician could select that all previous diagnoses in the patient's electronic medical records be retested and/or monitored.

Upon deciding ailment(s) of interest, the physician can set up (program) the Physician Application 150, or load a pre-existing interface setup, such as using the biomarkers as described below, to determine if the patient test data is indicative of the ailment of interest. To this end, the physician also can access the Digital Library 105 and search at step 420 for the ailment of interest (e.g., depression). The search typically returns published literature which provides data relations at step 430 that, when statistically compared to a base group of control subjects, has been shown to indicate the ailment. The physician can review the published literature and decide at step 440 whether to accept or reject the data relations in a particular article. If the physician rejects the data relation, then the Physician Application 150 is not updated at step 450. In addition to searching for published literature which indicates data relations for a particular ailment, the physician can use personal knowledge about patient test data to set up data relations to be compared to the control group at step 470. Still yet, the physician can search for and load pre-designed expert interfaces (biomarkers) with data relations that have been developed by experts in the field at step 480. Whether the physician selects data relations from the Digital Library 105, enters data relations based on personal knowledge, and/or accepts a pre-designed expert interface, the application interface is appropriately updated.

Use Of Biomarkers On Patient Data

The creation of biomarkers provides the physician with the tools that can be used to analyze complex and voluminous collected patient data in order to identify one or more conditions relating to the patient. FIG. 5 illustrates diagrammatically the use of the biomarker concept. The plane on the left of the Figure labeled "Data" represents a data matrix of collected patient data points (shown as the "X"s in the 11 Rows R1-R11 and 11 columns C1-C11 of FIG. 5 for illustrative purposes) for a selected patient and stored in Patient_Test_Data Module 340. This can be test measurement data, such as the above-described EEG data, which can optionally include patient characterization data (mentioned above), which can also optionally include data from related tests as stored in Medical Data Input Module 360.

The physician can manipulate the collected patient data (DATA) with Physician Diagnosis Module 390 at step 1601 by retrieving the stored collected patient test data from memory, such as Patient_Test_Data Module 340 and using any of a number of predefined mathematical and/or logical processes, termed "biomarkers" herein. At step 1602, the physician can select one or more desired biomarkers (Process A, Process B), which are used to manipulate the collected patient data (DATA). The order of data manipulation by these biomarkers is also selected by the physician at step 1603, with series or parallel or combinations of series and parallel processing being possible. In FIG. 5, the biomarker data manipulation processes (Process A, Process B) are illustrated as planes which are parallel to the collected patient data plane (DATA). The data flows from left to right, with each data point (X) in the matrix of collected patient data (DATA) being operated on (in some cases ignored) at step 1604 by each successive biomarker process (Process A, Process B) to produce "O"s, then "□"s; thence the resultant output data set (DISPLAY) of "D"s which is indicative of the biomarker(s) extracted from the collected patient data is stored at step 1605 by the Physician Diagnosis Module 390. By comparing the extracted biomarker(s) with standard biomarkers associated with known ailments, the physician can ascertain what ailment(s) are likely impacting the selected patient. This comparison can be executed by Physician Diagnosis Module 390 at step 1606, or the biomarker results can be presented at step 1607 as multi-dimensional visualizations which can be concurrently displayed at step 1608 on display 120 with standard visualizations of biomarkers associated with ailments.

Therefore, the physician can access a library of biomarker data manipulation processes and test the diagnosis hypothesis on the collected patient data (DATA) to see what results are obtained. When the output data (DISPLAY) produces a recognizable pattern matching a known set of biomarkers for a defined ailment, the physician can then have confidence that their hypothesis is credible. Since the collected patient data (DATA) is unlikely to have a 100% correlation with any selected biomarker, the biomarkers can be defined as "fuzzy filters" which have a range of typical values or weights assigned to various processes and/or data points thereby to capture ailments where the data may not be conclusive, but also not totally reject data that are not accurate matches to the known ailment archetype data.

In some cases, the physician selects only a portion of the data collected to be analyzed and/or displayed. For example, if a large amount of EEG data is collected under a variety of test conditions, the physician could select the portion of the EEG data for analysis that is desired by the physician.

The collection of biomarkers for ailments can be stored in the Patient Data Management System 300 or can be stored in whole or in part in the Digital Library 105 for retrieval by the physician. The Digital Library physician interface screen can be generated that also presents articles, links to articles, summaries of articles, or other published information retrieved from the Digital Library 105. The Digital Library physician interface screen allows the physician to search Digital Library 105 for data relations relating to particular ailments and/or conditions of interest to the physician. For example, the physician could search for data relations which might indicate Alzheimer's, ADD, depression, or the like when statistically compared to the normal EEG data stored in normative database 260. Once an analysis of the data relations has been performed, the Report Physician Interface Screen can be displayed on the terminal. The Report Physician Interface Screen could include a predictive ailment report containing a list of potential mental or physical ailments and/or a treatment report containing treatment plans for the list of potential mental or physical ailments in the predictive ailment report. The Diagnostic Physician Interface Screen can be displayed on the terminal with input and/or selection areas that allows for a physician to input a diagnosis, the physician's reasoning, and/or prescribed treatment plans.

Typical EEG Output Data Visualizations

Figure 13A:
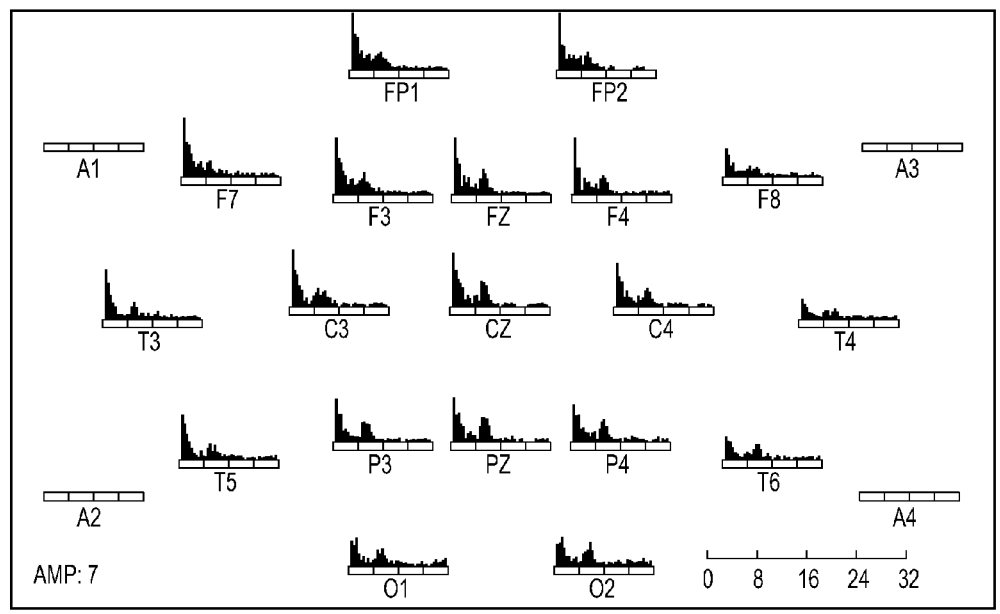
FIG. 13A is a screen shot of EEG data presented in a spectral array.
Figure 13B:
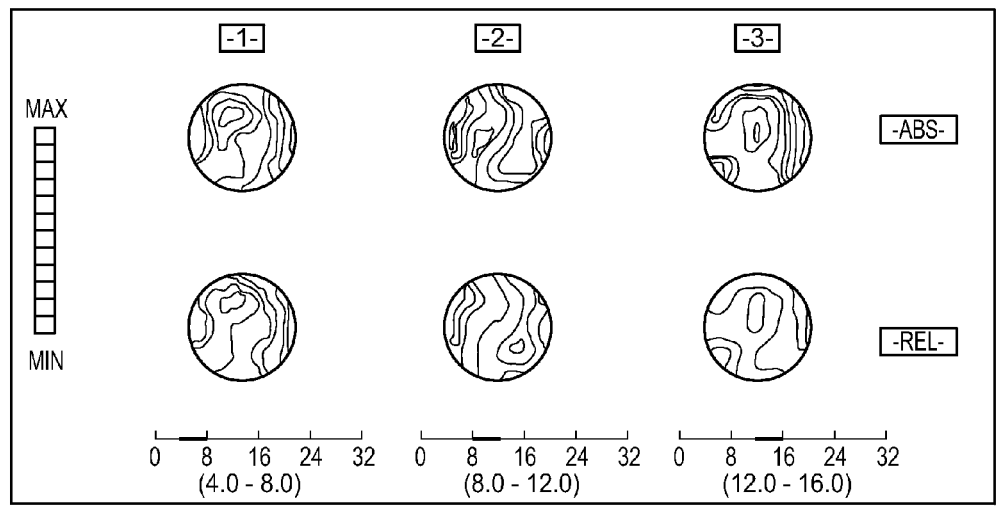
FIG. 13B is a screen shot of topographic maps of the raw EEG data.
Figure 14A:
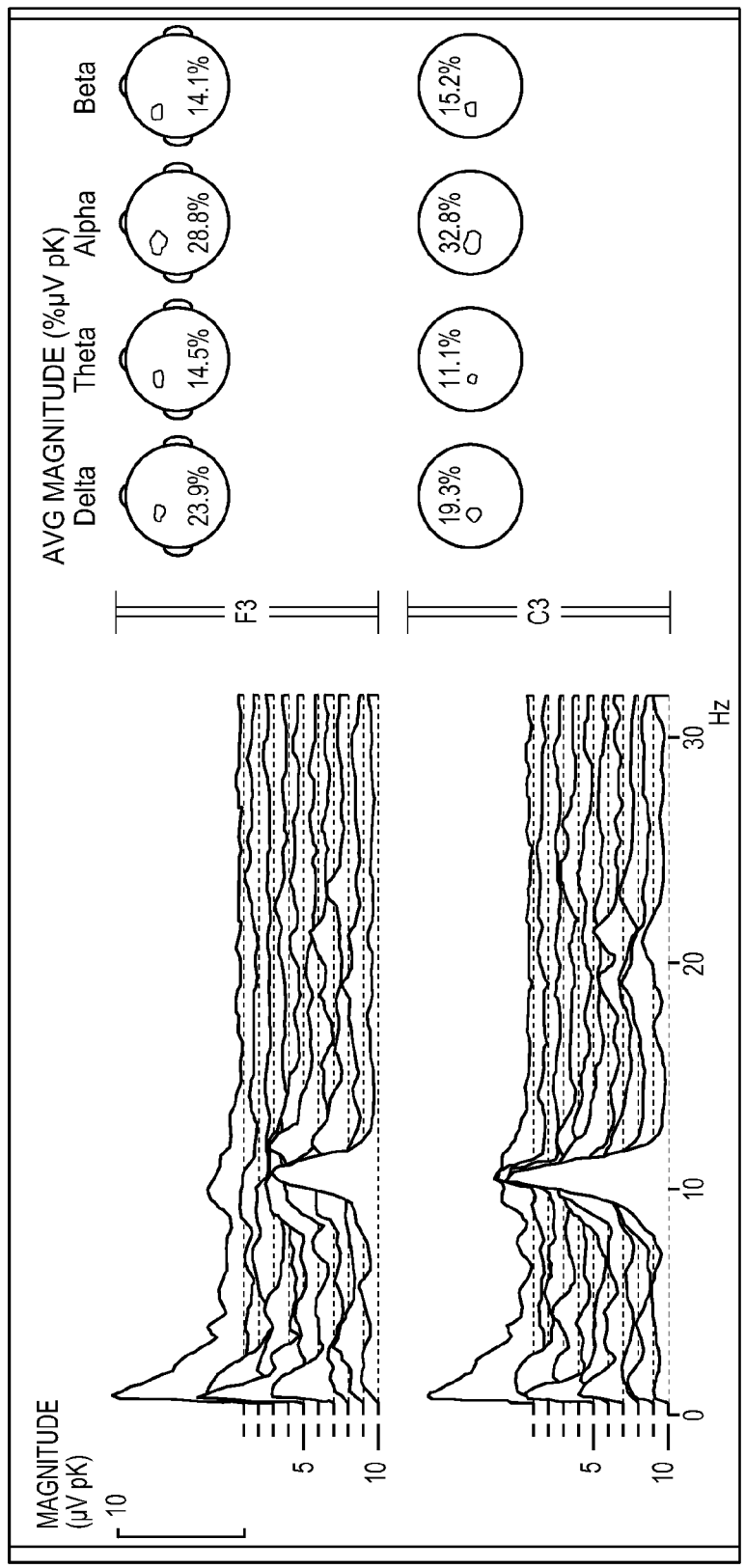
FIG. 14A illustrates a screen shot showing a compressed spectral array of raw EEG data.
Figure 14B:
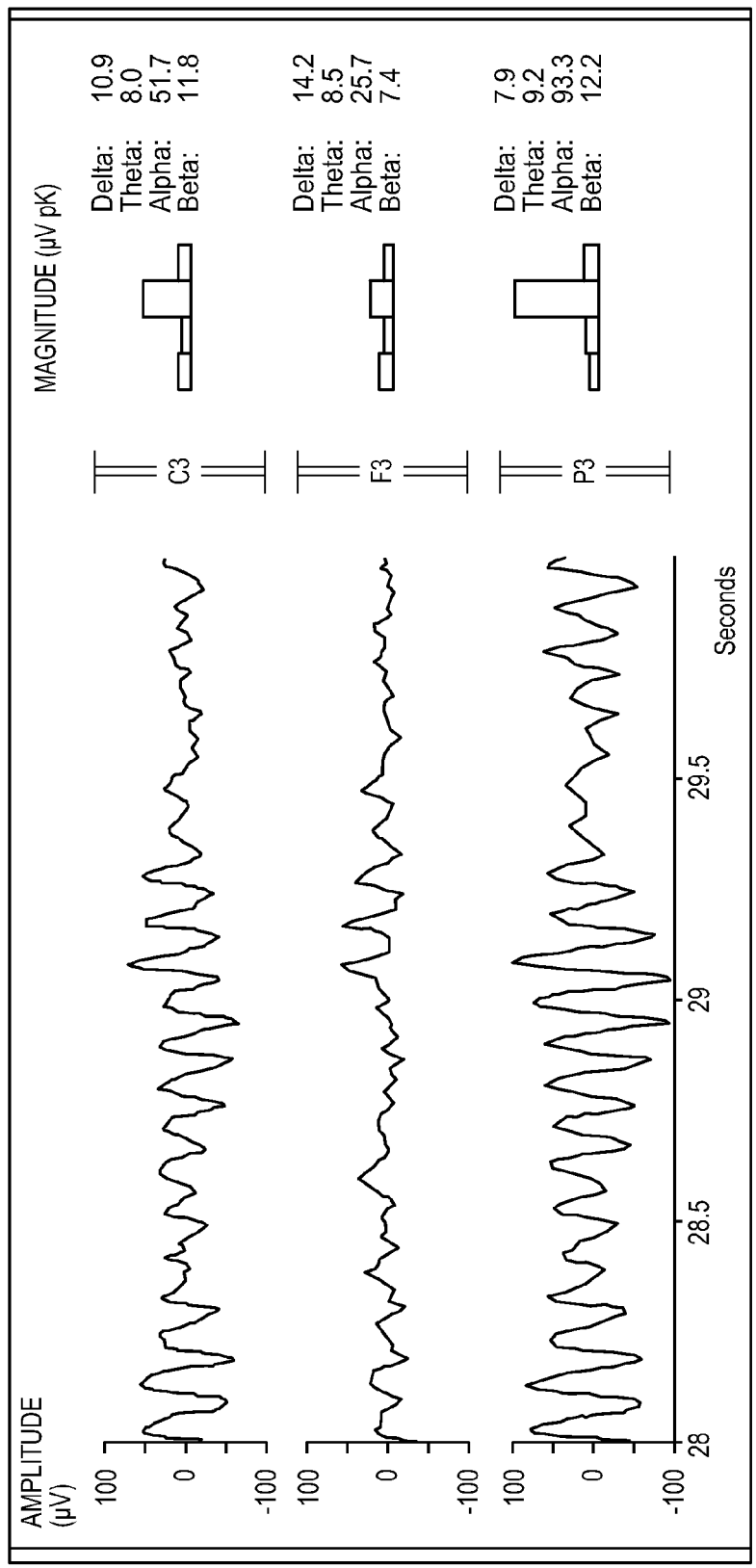
FIG. 14B illustrates a screen shot of a trend analysis of the raw EEG data.

FIG. 13A is a screen shot of patient EEG test data presented in a spectral array that may be presented. To generate the spectral array shown in FIG. 13A, the raw EEG waves for each electrode are transformed into magnitude or power spectrums. From this type of display, a trained clinician could derive the distribution of power and amplitude (strength) of the brainwaves at each site. FIG. 14B is a screen shot of topographic maps of the raw EEG data that may be presented. As illustrated in FIG. 14B, the topographic maps summarize EEG data by representing power values (i.e., voltage variations) in selected frequencies at selected electrode sites.

Figure 15:
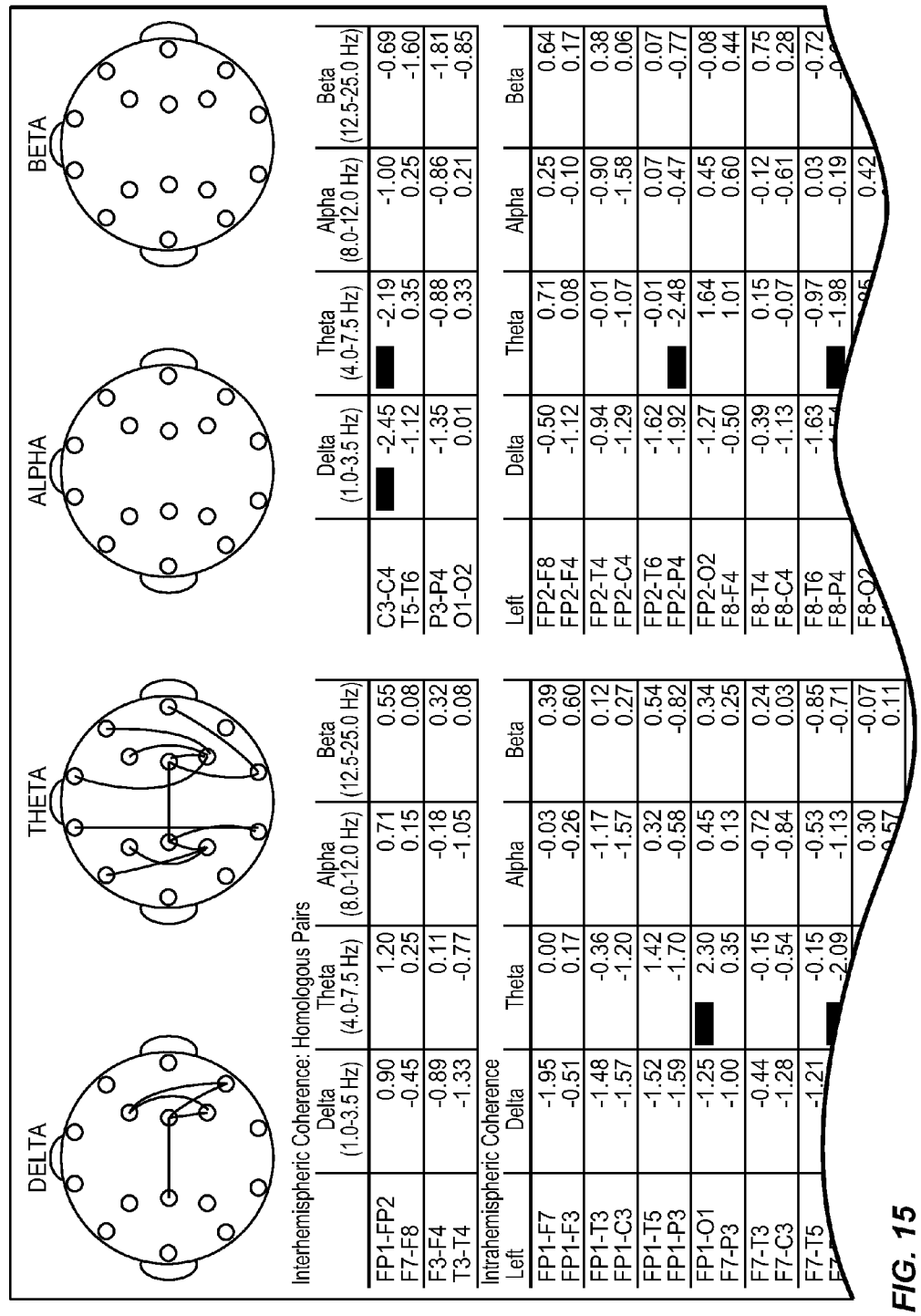
FIG. 15 illustrates the operation of the Patient Data Management System in manipulating collected patient data.

FIG. 15 illustrates a screen shot showing a compressed spectral array of raw EEG data that may be presented. The compressed spectral array illustrates how the spectrum of EEG evolves over time and can be useful for demonstrating certain trends in the data over time which is not observable in many of the other display formats.

Summary

The Patient Data Management System enables a physician to select predetermined (or physician defined) data manipulation processes, illustrative of predetermined ailment biomarkers, to be used in manipulating collected patient data to thereby obtain results which can be visualized to confirm or deny the validity of the physician's diagnosis.

What is claimed as new and desired to be protected by Letters Patent of the United States is:

1. A physician operated medical data analysis system for assisting a physician in identifying ailments and conditions relating to an identified patient, comprising:

a memory for storing:

a plurality of sets of patient medical data relating to an identified patient, which patient medical data comprises a plurality of measurements of biomarkers that correspond to a biological property of one or more organisms in the patient, a plurality of sets of ailment-specific biomarkers, each of which correspond to a set of characteristic biological properties that can be detected and measured in a patient, and each of which are indicative that an organism is afflicted with a predetermined ailment, and a plurality of data manipulation modules, each defining at least one process for transforming patient medical data pursuant to a predefined schema to produce a set of biomarkers that are indicative of selected biological properties of at least one organism in the patient;

a patient medical data processor, responsive to a physician selecting one of said plurality of stored sets of patient medical data, a plurality of the stored data manipulation modules and an order of applying the selected plurality of stored data manipulation modules to the selected stored set of patient medical data, for processing the selected patient medical data using the selected data manipulation modules in the selected order to produce an output set of patient-specific biomarkers that are indicative of biological properties of at least one organism in the patient;

a patient data manipulation module, responsive to the physician selecting a plurality of sets of ailment-specific biomarkers via the physician terminal device, configured to identify said patient-specific biomarkers in said output set of patient-specific biomarkers that correlate with each of the biomarkers in each of the selected sets of ailment-specific biomarkers; and a display device for displaying on a physician terminal device for visual comparison, a visualization of each of the plurality of sets of ailment-specific biomarkers selected by the physician and a visualization of the identified patient-specific biomarkers.

2. The medical data analysis system of claim 1 wherein the set of patient medical data comprises:
monitoring data collected from medical devices operable to measure physiological data relating to the identified patient.

3. The medical data analysis system of claim 1 wherein each of the plurality of data manipulation modules comprises:
at least one mathematical or logical data manipulation schema for transforming an input set of data pursuant to predefined data manipulation rules to identify a correspondence of a predetermined biomarker with patient medical data in the selected set of patient medical data.

4. The medical data analysis system of claim 1 wherein the patient medical data processor comprises:
a condition identification process, for generating an indication of a degree of correspondence between a predetermined biomarker associated with the data manipulation module and the selected set of patient medical data to identify a probability of a condition defined by the selected data manipulation module being present in the selected patient.

5. The medical data analysis system of claim 1, further comprising:
a comparative display generator for generating a visualization of both the selected patient medical data and the predetermined biomarker associated with a condition.

6. A method of operating a physician operated medical data analysis system for assisting a physician in identifying ailments and conditions relating to an identified patient, comprising:
storing in a memory:
at least one set of patient medical data relating to an identified patient, which patient medical data comprises a plurality of measurements of biomarkers that correspond to a biological property of one or more organisms in the patient,
a plurality of sets of ailment-specific biomarkers, each of which correspond to a set of characteristic biological properties that can be detected and measured in a patient, and each of which are indicative that an organism is afflicted with a predetermined ailment, and
enabling a physician to access, via a user interface communicatively connected to a server, a plurality of data manipulation modules, each defining at least one process for transforming said patient medical data pursuant to a predefined schema to produce a set of biomarkers that are indicative of selected biological properties of at least one organism in the patient;
processing in a server, in response to a physician selecting a set of patient medical data, a plurality of the data manipulation modules and an order of applying the selected data manipulation modules to the selected patient medical data, the selected patient medical data using the selected data manipulation modules in the selected order to produce an output set of patient-specific biomarkers that are indicative of biological properties of at least one organism in the patient;
identify, in response to the physician selecting a plurality of sets of ailment-specific biomarkers via the physician terminal device, said patient-specific biomarkers in said output set of patient-specific biomarkers that correlate with each of the biomarkers in each of the selected sets of ailment-specific biomarkers; and
presenting, on a display communicatively connected to the server, a visualization of each of the plurality of sets of ailment-specific biomarkers selected by the physician and a visualization of the output set of patient-specific biomarkers.

7. The method of operating a medical data analysis system of claim 6, further comprising:
collecting monitoring data from medical devices operable to measure physiological data relating to the identified patient.

8. The method of operating a medical data analysis system of claim 6 wherein the step of processing patient medical data comprises:
transforming, using at least one mathematical or logical data manipulation schema defined by the data manipulation module, an input set of data pursuant to predefined data manipulation rules to identify a correspondence of a predetermined biomarker in the selected set of patient medical data.

9. The method of operating a medical data analysis system of claim 8 wherein the step of processing patient medical data comprises:
generating an indication of a degree of correspondence between a predetermined biomarker associated with the data manipulation module and the selected set of patient medical data to identify a probability of a condition defined by the selected data manipulation module being present in the selected patient.

10. The method of operating a medical data analysis system of claim 6, further comprising:
generating a visualization of both the selected patient medical data and the predetermined biomarker associated with a condition.

11. A physician operated medical data analysis system for assisting a physician in identifying ailments and conditions, relating to an identified patient, via an associated set of patient medical data, comprising:
a plurality of data manipulation modules, each defining at least one process for transforming said patient medical data relating to an identified patient, which patient medical data comprises a plurality of measurements of biomarkers that correspond to a biological property of one or more organisms in the patient pursuant to a predefined schema to a set of biomarkers that are indicative of selected biological properties of at least one organism in the patient;
a patient medical data processor, responsive to a physician selecting a data manipulation module for application to a set of patient medical data, for processing the set of patient medical data using the selected data manipulation module to produce an output set of patient-specific biomarkers that are indicative of biological properties of at least one organism in the patient;
a patient data manipulation module, responsive to the physician selecting a plurality of sets of ailment-specific biomarkers via the physician terminal device, configured to identify said patient-specific biomarkers in said output set of patient-specific biomarkers that correlate with each of the biomarkers in each of the selected sets of ailment-specific biomarkers; and
a display, communicatively connected to the patient medical data processor, for presenting a visualization of each of the plurality of sets of ailment-specific biomarkers selected by the physician and a visualization of the output set of patient-specific biomarkers.

12. The medical data analysis system of claim 11 wherein the set of patient medical data comprises:
  monitoring data collected from medical devices operable to measure physiological data relating to the identified patient.

13. The medical data analysis system of claim 11 wherein each of the plurality of data manipulation modules comprises:
  at least one mathematical or logical data manipulation schema for transforming an input set of data pursuant to predefined data manipulation rules to identify a correspondence of a predetermined biomarker with patient medical data in the selected set of patient medical data.

14. The medical data analysis system of claim 11 wherein the patient medical data processor comprises:
  a condition identification process, for generating an indication of a degree of correspondence between a predetermined biomarker associated with the data manipulation module and the selected set of patient medical data to identify a probability of a condition defined by the selected data manipulation module being present in the selected patient.

15. The medical data analysis system of claim 11, further comprising:
  a comparative display generator for generating a visualization of both the selected patient medical data and the predetermined biomarker associated with a condition.

16. A method of operating a physician operated medical data analysis system for assisting a physician in identifying ailments and conditions, relating to an identified patient, via an associated set of patient medical data, comprising:
  enabling a physician to access a plurality of data manipulation modules, each defining at least one process for transforming said patient medical data relating to an identified patient, which patient medical data comprises a plurality of measurements of biomarkers that correspond to a biological property of one or more organisms in the patient pursuant to a predefined schema to a set of biomarkers that are indicative of selected biological properties of at least one organism in the patient;
  processing in a server, in response to a physician selecting a data manipulation module for application to a set of patient medical data, for processing the set of patient medical data using the selected data manipulation module to produce an output set of patient-specific biomarkers that are indicative of biological properties of at least one organism in the patient; and
  presenting, on a display communicatively connected to the server, a visualization of each of the plurality of sets of ailment-specific biomarkers selected by the physician and a visualization of the output set of patient-specific biomarkers.

17. The method of operating a medical data analysis system of claim 16, further comprising:
  collecting monitoring data from medical devices operable to measure physiological data relating to the identified patient.

18. The method of operating a medical data analysis system of claim 16 wherein the step of processing patient medical data comprises:
  transforming, using at least one mathematical or logical data manipulation schema defined by the data manipulation module, an input set of data pursuant to predefined data manipulation rules to identify a correspondence of a predetermined biomarker in the selected set of patient medical data.

19. The method of operating a medical data analysis system of claim 18 wherein the step of processing patient medical data comprises:
  generating an indication of a degree of correspondence between a predetermined biomarker associated with the data manipulation module and the selected set of patient medical data to identify a probability of a condition defined by the selected data manipulation module being present in the selected patient.

20. The method of operating a medical data analysis system of claim 16, further comprising:
  generating a visualization of both the selected patient medical data and the predetermined biomarker associated with a condition.

* * * * *